US006995251B1

United States Patent
Matzuk et al.

(10) Patent No.: US 6,995,251 B1
(45) Date of Patent: Feb. 7, 2006

(54) OVARY-SPECIFIC GENES AND PROTEINS

(75) Inventors: Martin M. Matzuk, Pearland, TX (US); Pei Wang, Houston, TX (US)

(73) Assignee: Baylor, Houston, TX (US)

( * ) Notice: Subject to any disclaimer, the term of this patent is extended or adjusted under 35 U.S.C. 154(b) by 0 days.

(21) Appl. No.: 09/830,810

(22) PCT Filed: Oct. 28, 1999

(86) PCT No.: PCT/US99/25209

§ 371 (c)(1),
(2), (4) Date: Jul. 25, 2001

(87) PCT Pub. No.: WO00/24755

PCT Pub. Date: May 4, 2000

Related U.S. Application Data

(60) Provisional application No. 60/106,020, filed on Oct. 28, 1999.

(51) Int. Cl.
*C07H 21/00* (2006.01)
(52) U.S. Cl. ............... 536/23.5; 435/252.3; 435/320.1; 435/325
(58) Field of Classification Search ................ 530/350
See application file for complete search history.

(56) References Cited

U.S. PATENT DOCUMENTS

| | | | |
|---|---|---|---|
| 5,547,854 A | 8/1996 | Donahoe et al. | |
| 5,563,059 A | 10/1996 | Alak et al. | |
| 5,661,126 A | 8/1997 | Donahoe et al. | |
| 5,801,016 A | 9/1998 | Morioka et al. | |

FOREIGN PATENT DOCUMENTS

| | | |
|---|---|---|
| WO | WO-94/15966 | 7/1994 |
| WO | WO98/40483 | 9/1998 |
| WO | WO-00/24755 A1 | 5/2000 |

OTHER PUBLICATIONS

Elvin, Julia A., et al.; Paracrine Actions of Growth Differentiatin Factor-9 in the Mammalian Ovary; Molecular Endocrinology, vol. 13, No. 6, 1999.
Elvin, Julia A., et al.; Molecular Characterization of the Follicle Defects in the Growth Differentiation Factor 9-Deficient Ovary; Molecular Endocrinology, vol. 13, No. 6; 1999.
Matzuk, Martin M., et al.; Transgenic Models to Study the Roles of Inhibins and Activins in Reproduction, Oncogenesis, and Development; Recent Progress in Hormone Research, vol. 51.
Ohsumi, Keita, et al.; Characterization of the Ooplasmic Factor Inducing Decondensation of and Protamine Removal from Toad Sperm Nuclei: Involvement of Nucleoplasmin; Developmental Biology; vol. 148; 1991.
Philpott, Anna, et al.; Nucleoplasmin Remodels Sperm Chromatin in Xenopus Egg Extracts; Cell; vol. 69; 1992.
Matzuk, Martin M., et al.; Different phenotypes for mice deficient in either activins or activin receptor type II; Nature; vol. 374; 1995.
Dong, Jinwen, et al.; Growth differentiation factor-9 is required during early ovarian folliculogenesis; Nature; vol. 383; 1996.
McGrath, Sharon A., et al.; Oocyte-Specific Expression of Growth/Differentiation Factor-9; Molecular Endocrinology; vol. 9, No. 1; 1995.
Kumar, T. Rajendra, et al.; Follicle stimulating hormone is required for ovarian follicle maturation but not male fertility; Nature Genetics; vol. 15; 1997.
Perreault, Sally D.; Chromatin remodeling in mammalian zygotes; Mutation Research; vol. 296; 1992.
Krohne, Georg, et al.; Immunological identification and localization of the predominant nuclear protein of the amphibian oocyte nucleus; Proc. Natl. Acad. Sci. USA; vol. 77; 1980.
Matzuk, Martin M . et al.; a Inhibin is a tumour-suppressor gene with gonadal specificity in mice; Nature; vol. 360; 1992.
Elvin, Julia A., et al.; Growth differentiation factor-9 stimulates progesterone synthesis in granulosa cells via a prostaglandin E2/EP2 receptor pathway; PNAS; vol. 97, No. 18; 2000.

(Continued)

*Primary Examiner*—Jon Weber
*Assistant Examiner*—Anand Desai
(74) *Attorney, Agent, or Firm*—Fulbright & Jaworski L.L.P.

(57) ABSTRACT

Ovary-specific proteins O1-180, O1-184 and O1-236, polynucleotides encoding them, antibodies which are immunoreactive with them and vectors and host cells containing O1-180, O1-184 or O1-236 are provided. Also provided are methods for detecting cell proliferative or degenerative disorders of ovarian origin and which are associated with O1-180, O1-184 or O1-236. Further provided are methods for the evaluation of potential contraceptives using the proteins of the invention, as well as methods for the screening for genetic mutations in signaling pathways that are associated with some forms of human infertility or gynecological cancers, also using the proteins/mRNAs/genes of the invention. The proteins/mRNAs/genes of the invention may also be used as markers for identifying primary and metastatic neoplasms of ovarian origin and as indicators of developmental anomalies in prenatal screening procedures. Furthermore, assays of the proteins/mRNAs/genes of the invention can be used in diagnostic assays for detecting forms of infertility and other diseases, including germ cell tumors and polycystic ovary syndrome. The proteins of the invention may be useful targets for in vitro fertilization procedures or in enhancing the number of eggs that can be retrieved from the human donor, e.g., in enhancing the success rate.

9 Claims, 15 Drawing Sheets

OTHER PUBLICATIONS

MacArthur, Craig A., et al.; Npm3: A Novel, Widely Expressed Gene Encoding a Protein Related to the Molecular Chaperones Nucleoplasmin and Nucleophosmin; Genomics; vol. 42; 1997.

Mills, A. D., et al.; An Acidic Protein Which Assembles Nucleosomes in Vitro is the Most Abundant Protein in Xenopus Oocyte Nuclei; J. Mol. Biol.; vol. 139; 1980.

Dingwall, Colin, et al.; Nucleoplasmin cDNA sequence reveals polyglutamic acid tracts and a cluster of sequences homologous to putative nuclear localization signals; The EMBO Journal; vol. 6, No. 1; 1987.

McLay, David W., et al.; The Ability to Organize Sperm DNA into Functional Chromatin Is Acquired during Meiotic Maturation in Murine Oocytes; Developmental Biology; vol. 186; 1997.

Carabatsos, Mary Jo, et al.; Characterization of Oocyte and Follicle Development in Growth Differentiation Factor-9-Devicient Mice; Developmental Biology; vol. 204; 1998.

Philpott, Anna, et al.; Sperm Decondensatino In Xenopus Egg Cytoplasm Is Mediated by Nucleoplasmin; Cell; vol. 65; 1991.

Burglin, Thomas R., et al.; Cloning of nucleoplasmin from Xenopus laevis oocytes and analysis of its developmental expression; Genes & Development; vol. 1; 1987.

Wu, X., et al.; Zygote arrest 1 (Zar1) is a novel maternal-effect gene critical for the oocyte-to-embryo transition; Nat Genet. 33(2):187-191, Feb. 2003.

Matzuk, M.M., et al.; Genetic dissection of mammalian fertility pathways; Nat Cell Biol. Suppl 4:S41-49, Oct. 2002.

Varani, S., et al.; Phenotypic effects of knockout of oocyte-specific genes; Ernst Schering Res Found Workshop (41): 63-79, 2002.

Matzuk, M. M., et al.; Intercellular communication in the mammalian ovary: oocytes carry the conversation. Science 296 (5576):2178-2180; Jun. 21, 2002.

Rajkovic, A., et al.; Functional analysis of oocyte-expressed genes using transgenic models. Mol Cell Endocrinol. 187 (1-2):5-9, Feb. 22, 2002.

Yan, C., et al.; Oosp1 encodes a novel mouse oocytesecreted protein; Genesis 31(3):105-110, Nov. 2001.

Lau, A., et al.; Transgenic models in the study of reproduction; Gravit Space Biol Bull. 12(2):75-82, May 1999.

Elvin, J.A., et al.; Oocyte-expressed TGF-beta superfamily members in female fertility; Mol Cell Endocrinol 159(1-2): 1-5, Jan. 25, 2000.

The Sanger Centre, et al.; Toward a Complete Human Genome Sequence; Genome Research 8:1097-1108, 1998.

Ringuette, Maurice et al, "Oocyte-specific gene expressio: Moleculat characterization of a cDNA coding for ZP-3, the sperm receptor of the mouse zona pellucida," Proc. Natl. Acad. Sci. vol. 83, pp. 4341-4345, Jun. 1986.

Gene name: O1-180 cDNA sequence: 1276 bp

"AAGGCGGGCGAGGCGCGGGACGCACCCATGTTCCCGGCGAG
CACGTTCCACCCCTGCCCGCATCCTTATCCGCAGGCCACCAAAGCCGGGGATG
GCTGGAGGTTCGGAGCCAGGGGCTGCCGACCCGCGCCCCCTCCTTCCTCCCC
GGCTACAGACAGCTCATGGCCGCGGAGTACGTCGACAGCCACCAGCGGGCAC
AGCTCATGGCCCTGCTGTCGCGGATGGGTCCCCGGTCGGTCAGCAGCCGTGA
CGCTGCGGTGCAGGTGAACCCGCGCCGCGACGCCTCGGTGCAGTGTTCACTC
GGGCGCCGCACGCTGCAGCCTGCAGGGTGCCGAGCCAGCCCCGACGCCCGAT
CGGGTTCCTGTCAACCCCGTGGCCACGCCGGCGCCGGGAGATCCCCGCGATC
CTGGCAGACCGTAGCCCCGTTCTCGTCCGTGACCTTCTGTGGCCTCTCCTCCTC
ACTGGAGGTTGCGGGAGGCAGGCAGACACCCACGAAGGGAGAGGGGAGCCC
GGCATCCTCGGGGACCCGGGAACCGGAGCCGAGAGAGGTGGCCGCGAGGAA
AGCGGTCCCCCAGCCGCGAAGCGAGGAGGGCGATGTTCAGGCTGCAGGGCA
GGCCGGGTGGGAGCAGCAGCCACCACCGGAGGACCGGAACAGTGTGGCGGC
GATGCAGTCTGAGCCTGGGAGCGAGGAGCCATGTCCTGCCGCAGAGATGGCT
CAGGACCCCGGTGATTCGGATGCCCCTCGAGACCAGGCCTCCCCGCAAAGCAC
GGAGCAGGACAAGGAGCGCCTGCGTTTCCAGTTCTTAGAGCAGAAGTACGGCT
ACTATCACTGCAAGGACTGCAAAATCCGGTGGGAGAGCGCCTATGTGTGGTGT
GTGCAGGGCACCAGTAAGGTGTTACTTCAAACAGTTCTGCCGAGTGTGTGAGAA
ATCCTACAACCCTTACAGAGTGGAGGACATCACCTGTCAAAGTTGTAAAAGAAC
TAGATGTGCCTGCCCAGTCAGATTTCGCCACGTGGACCCTAAACGCCCCCATC
GGCAAGACTTGTGTGGGAGATGCAAGGACAAACGCCTGTCCTGCGACAGCAC
CTTCAGCTTCAAATACATCATTTAGTGAGAGTCGAAAACGTTTCTGCTAGATGG
GGCTAATGGAATGGACAAGTGAGCTTTCTCCCTCTTCACCTCTTCCCTTTCCAA
ATTCTTCATGACAGACAGTGTTACTTGGATATAAAGCCTGTGAATAAAAGGTAT
TGCAAACAAAAAAAAAAAAAAAAAA"

Figure 1

Amino Acid sequence: 361aa

"MFPASTFHPCPHPYPQATKAGDGWRFGARGCRPAPPSFLPGYRQLMAAEYVDS
HQRAQLMALLSRMGPRSVSSRDAAVQVNPRRDASVQCSLGRRTLQPAGCRASPDA
RSGSCQPRGHAGAGRSPRSWQTVAPFSSVTFCGLSSSLEVAGGRQTPTKGEGSPA
SSGTREPEPREVAARKAVPQPRSEEGDVQAAGQAGWEQQPPPEDRNSVAAMQSEP
GSEEPCPAAEMAQDPGDSDAPRDQASPQSTEQDKERLRFQFLEQKYGYYHCKDCK
IRWESAYVWCVQGTSKVYFKQFCRVCEKSYNPYRVEDITCQSCKRTRCACPVRFR
HVDPKRPHRQDLCGRCKDKRLSCDSTFSFKYII"

Figure 2

O1-184 cDNA sequence: 1817bp

```
GTCACAGCTTTCCCCTGCCCGAATATGGTGATCTGTCTCCATTGTCCAGATCA
GGATGATTCTTTAGAAGAAGTCACAGAGGAATGCTATTCCCCACCCACCCTC
CAGAACCTGGCAATTCAGAGTCTACTGAGGGATGAGGCCTTGGCCATTTCTG
CTCTCACGGACCTGCCCCAGAGTCTGTTCCCAGTAATTTTTGAGGAGGCCTTC
ACTGATGGATATATAGGGATCTTGAAGGCCATGATACCTGTGTGGCCCTTCCC
ATACCTTTCTTTAGGAAAGCAGATAAATAATTGCAACCTGGAGACTTTGAAG
GCTATGCTTGAGGGACTAGATATACTGCTTGCACAAAAGGTTCAAACCAGTA
GGTGCAAACTCAGAGTAATTAATTGGAGAGAAGATGACTTGAAGATATGGGC
TGGATCCCATGAAGGTGAAGGCTTACCAGATTTCAGGACAGAGAAGCAGCCA
ATTGAGAACAGTGCTGGCTGTGAGGTGAAGAAAGAATTGAAGGTGACGACT
GAAGTCCTTCGCATGAAGGGCAGACTTGATGAATCTACCACATACTTGTTGC
AGTGGGCCCAGCAGAGAAAAGATTCTATTCATCTATTCTGTAGAAAGCTACT
AATTGAAGGCTTAACCAAAGCCTCAGTGATAGAAATCTTCAAAACTGTACAC
GCAGACTGTATACAGGAGCTTATCCTAAGATGTATCTGCATAGAAGAGTTGG
CTTTTCTTAATCCCTACCTGAAACTGATGAAAGTCTTTTCACACTCACACTA
GATCACATCATAGGTACCTTCAGTTTGGGTGATTCTGAAAAGCTTGATGAGG
AGACAATATTCAGCTTGATTTCTCAACTTCCCACACTCCACTGTCTCCAGAAA
CTCTATGTAAATGATGTCCCTTTTATAAAAGGCAACCTGAAAGAATACCTCAG
GTGCCTGAAAAAGCCCTTGGAGACACTTTGCATCAGTAACTGTGACCTCTCAC
AGTCAGACTTGGATTGCCTGCCCTATTGCCTGAATATTTGTGAACTCAAACAT
CTGCATATTAGTGATATATATTTATGTGATTTACTCCTTGAGCCTCTTGGTTTT
CTCCTTGAGAGAGTTGGAGATACCCTGAAAACCCTGGAATTGGATTCATGTT
GTATAGTGGACTTTCAGTTCAGTGCCTTGCTGCCTGCCCTAAGCCAATGTTCT
CACCTCAGAGAGGTCACTTTCTATGATAATGATGTTTCTCTGCCTTTCTTGAA
AACAACTTCTACACCACACAGCCCTGCTGAGTCAGCTGATCTATGAGTGTTAC
CCTGCCCCTCTAGAGTGCTATGATGACAGTGGTGTAATACTAACACACAGATT
AGAAAGTTTTTGTCCTGAGCTTCTGGATATACTGAGAGCCAAAAGACAGCTC
CATAGTGTCTCCTTTCAAACAACCAAATGCTCTAAATGTGGTGGGTGCTACAT
TTATGATCGGCATACCCAATGTTGCCGTTTTGTGGAACTACTATAAGCTTGAT
TGTGAAACTGAGAAATAGAAACTTAGTATTGGGGACTGATGAAATCCTAAGT
GAATGTCCACTGCTAAATGGAGCATGAAAATGTCAATCACCTAAAAGTCTGA
GATACACAGGAAAGTCAATAACTTCCTCTGAGCTGGTGAATGGATGTTGCAT
CTGTAGAAAGTATCAAGCACTTGTAGTTTGAATGTGTTACAATAGAAGCACC
ATTTTATGAGACTGGCCCAATCTGTTGACTGCATACAATAAATCTGTTGACTT
ATTAAATTTTTAAAAAAAAAAAAAAAAAAAAAAA
```

Figure 3

O1-184 amino acid sequence: 426 amino acids

MVICLHCPDQDDSLEEVTEECYSPPTLQNLAIQSLLRDEALAISALTDLPQSLFP
VIFEEAFTDGYIGILKAMIPVWPFPYLSLGKQINNCNLETLKAMLEGLDILLAQKV
QTSRCKLRVINWREDDLKIWAGSHEGEGLPDFRTEKQPIENSAGCEVKKELKV
TTEVLRMKGRLDESTTYLLQWAQQRKDSIHLFCRKLLIEGLTKASVIEIFKTVHA
DCIQELILRCICIEELAFLNPYLKLMKSLFTLTLDHIIGTFSLGDSEKLDEETIFSLIS
QLPTLHCLQKLYVNDVPFIKGNLKEYLRCLKKPLETLCISNCDLSQSDLDCLPYC
LNICELKHLHISDIYLCDLLLEPLGFLLERVGDTLKTLELDSCCIVDFQFSALLPAL
SQCSHLREVTFYDNDVSLPFLKTTSTPHSPAESADL

Figure 4

Gene name: O1-236 cDNA sequence: 1019bp

"GCCATATTGAGGACCTGCAGTAGAGGTGGAACCCATGACTGGCAGCGCAAAC
ACAGTGATAACAGCTGAGCTCCAAGCAAGGACCCAGGACCTTGCCTCACCACA
GACATAATCTTTCCCCACAACACCTCCACCAAGCCGCCCTGTAAATCGACATGA
GTCGCCACAGCACCAGCAGCGTGACCGAAACCACAGCAAAAAACATGCTCTGG
GGTAGTGAACTCAATCAGGAAAGCAGACTTGCACCTTTAGAGGCCAAGGCGA
GAAGAAGGACAGCTGTAAACTCTTGCTCAGCACGATCTGCCTGGGGGAGAAAG
CCAAAGAGGAGGTGAACCGTGTGGAAGTCCTCTCCCAGGAAGGCAGAAAACC
ACCAATCACTATTGCTACGCTGAAGGCATCAGTCCTGCCCATGGTCACTGTGTC
AGGTATAGAGCTTTCTCCTCCAGTAACTTTTCGGCTCAGGACTGGCTCAGGACC
TGTGTTCCTCAGTGGCCTGGAATGTTATGAGACTTCGGACCTGACCTGGGAAG
ATGACGAGGAAGAGGAGGAAGAGGAGGAGGAAGAGGATGAAGATGAGGATG
CAGATATATCGCTAGAGGAGATACCTGTCAAACAAGTCAAAAGGGTGGCTCCC
CAGAAGCAGATGAGCATAGCAAAGAAAAGAAGGTGGAAAAAGAAGAGGATG
AAACAGTAGTGAGGCCCAGCCCTCAGGACAAGAGTCCCTGGAAGAAGGAGAA
ATCTACACCCAGAGCAAAGAAGCCAGTGACCAAGAAATGACCTCATCTTAGCAT
CTTCTGCGTCCAAGGCAGGATGTCCAGCAGCTGTGTTTTGGTGCAGGTGTCCA
GCCCCACCACCCTAGTCTGAATGTAATAAGGTGGTGTGGCTGTAACCCTGTAAC
CCAGCCCTCCAGTTTCCGGAGGTTTTTGGTGAAGAGCCCCCAGCAAGTTCGCC
TAGGGCCACAATAAAATTTGCATGATCAGGAAAAAAAAAAAAAAAAAAAAAAA
AAAAAAAAAAAA"

Figure 5

Amino Acid sequence: 207aa

"MSRH STSS VTETTA KNMLW GSELN QEKQTCTFRG QGEKKDSCKLLLSTICLGEK AKEEV NRVEVLSQEG RKPPITIATLKAS VLP M VTVSGIELS PPVTFRLRTG SGPVFL S GLECYETSDLTW EDD EEEEEEEEEE DEDEDADISLEEIPVKQVKR VAPQKQMSIAKK KK VEK EEDETVVRPS PQDKSPWKKEKSTPRAKKPVTKK"

Figure 6

```
Npm2    MSRHSTSSVTETTAK--NMLWGSELN-QEKQTCTFRGQG-EKKDSCKLLL
        |.  ||||     |   ...|| |||  .| |   |..  |.|  .||
Xnpm2   MA--STVSNTSKLEKPVSLIWGCELNEQDK-TFEFKVEDDEEKCEHQLAL PKC
47      STICLGEKAKEEVNRVEVLSQE-GRKPPITIATLKASVLPMVTVSGIELS
        |.|||.|||.| | ||...|||  .  .||||| |.|||.|. ||||.
48      RTVCLGDKAKDEFNIVEIVTQEEGAEKSVPIATLKPSILPMATMVGIELT PKC                    CK2
96      PPVTFRLRTGSGPVFLSGLECYETSDLTWEDDEEEEEEEEEEDEDEDADI
        ||||||..||||...||  .   | .|  ..|.||||||.|.| |
98      PPVTFRLKAGSGPLYISGQHVAMEEDYSWAEEEDEGEAEGEEEEEEED-
```

```
                                                    CK2
146     SLEEIPVKQVKRVAPQKQMSIAKKKKVEKEEDETVVRPSPQDKSPWKKEK
         .|||  ||| | |..  ||||..|| ||     ...  || |||  |
147     --QESPPKAVKRPAATKKAGQAKKKKLDKE-DE-----SSEEDSPTKKGK

196     STPRAKKPVTKK    207
         .. |..||..||
189     GAGRGRKPAAKK    200
```

Figure 11

Mouse *Npm2* Gene Sequences
acagcagaggtgatgctcagaaatcaagttttaacagagggccaggtg
cttctagagtaggaggggattgcacacctccccaccccctcctctttc
ccaggcttcttaacagcctgctgtgggaagctgaccttagatggagc
cctgaaGCCATATTGAGGACCTGCAGTAGAGGTGGAACCCATGACTGG
CAGCGCAgtaagcttgagcagg... intron 1 = 343bp
...ctttgcattactcagAACACAGTGATAACAGCTGAGCTCCAAGCA
AGGACCCAGGACCTTGCCTCACCACAGACATAATCTTTCCCCACAACA
CCTCCACCAAGCCGCCCTGTAAATCGAC ATG AGT CGC CAC AGC
```
                                       M   S   R   H   S
 1
```

```
    ACC AGC AGC GTG ACC GAA ACC ACA GCA AAA AAC ATG
 6   T   S   S   V   T   E   T   T   A   K   N   M
```

```
    CTC TGG Ggtaagggctaaggct... intron 2 = 134bp
18   L   W
```

```
    ...gtcttcgctgtgcagGT AGT GAA CTC AAT CAG GAA AAG
20                      G   S   E   L   N   Q   E   K
```

```
    CAG ACT TGC ACC TTT AGA GGC CAA TGC GAG AAG AAG
28   Q   T   C   T   F   R   G   Q   C   E   K   K
```

```
    GAC AGC TGT AAA CTC TTG CTC AGC ACGgtgggtgtctcc
40   D   S   C   K   L   L   L   S   T
```

```
    aa... intron 3 = 92bp ...catcacctttctcagATC
49                                           I
```

```
    TGC CTG GGG GAG AAA GCC AAA GAG GAG GTG AAC CGT
50   C   L   G   E   K   A   K   E   E   V   N   R
```

```
    GTG GAA GTC CTC TCC CAG GAA GGC AGA AAA CCA CCA
62   V   E   V   L   S   Q   E   G   R   K   P   P
```

```
    ATC ACT ATT GCT ACG CTG AAG GCA TCA GTC CTG CCC
74   I   T   I   A   T   L   K   A   S   V   L   P
```

```
    ATGgtgagtcttctctcc... intron 4 = 2.8kb ...agaa
86   M
```

```
    gggggacacagGTC ACT GTG TCA GGT ATA GAG CTT TCT
87              V   T   V   S   G   I   E   L   S
```

```
    CCT CCA GTA ACT TTT CGG CTC AGG ACT GGC TCA GGA
96   P   P   V   T   F   R   L   R   T   G   S   G
```

Figure 13A

```
      CCT GTG TTC CTC AGT GGC CTG GAA TGT TAT Ggtaagt
108    P   V   F   L   S   G   L   E   C   Y gtagccta... intron 5 = 1.35kb ...ggctacccattcc agAG ACT TCG GAC CTG ACC TGG GAA GAT GAC GAG GAA
118      E   T   S   D   L   T   W   E   D   D   E   E GAG GAG GAA GAG GAG GAG GAA GAG GAT GAA GAT GAG
130    E   E   E   E   E   E   E   E   D   E   D   E GAT GCA GAT ATA TCG CTA GAG GAG ATA CCT GTC AAA
142    D   A   D   I   S   L   E   E   I   P   V   K CAA GTC AAA AGG GTG GCT CCC CAG AAG CAG ATG AGC
154    Q   V   K   R   V   A   P   Q   K   Q   M   S ATA GCA AAGgtgggggggaaaagaa... intron 6 = 186bp
166    I   A   K ...tggtttttgttccagAAA AAG AAG GTG GAA AAA GAA
169                        K   K   K   V   E   K   E GAG GAT GAA ACA GTA GTG AGgtaattcatgcagtt...
176    E   D   E   T   V   V   R intron 7 = 0.5kb ... ctattccctttccagG CCC AGC
183                                      P   S CCT CAG GAC AAG AGT CCC TGG AAG AAG gtgagcaataag
185    P   Q   D   K   S   P   W   K   K aag... intron 8 = 92bp ...ctcttatctgcacagGAG
194                                            E AAA TCT ACA CCC AGA GCA AAG AAG CCA GTG ACC AAG
195    K   S   T   P   R   A   K   K   P   V   T   K

AAA TGA CCTCATCTTAGCATCTTCTGCGTCCAAGGCAGGATGTCCA
207    K   *

GCAGCTGTGTTCTGGTGCAGGTGTCCAGCCCCACCACCCTAGTCTGAA
      TGTAATAAGGTGGTGTGGCTGTAACCCTGTAACCCAGCCCTCCAGTTT
      CCGGAGGTTTTTGGTGAAGAGCCCCCAGCAAGTTCGCCTAGGGCCACA
      ATAAAATTTGCATGATCAGGacctccctctgcctcccctccctggat
      gggtctcctcgctgctgcgatagctcatgtgcccagcagagggcaacc
      acgagcaagaaaccagccccatgt
```

Figure 13B

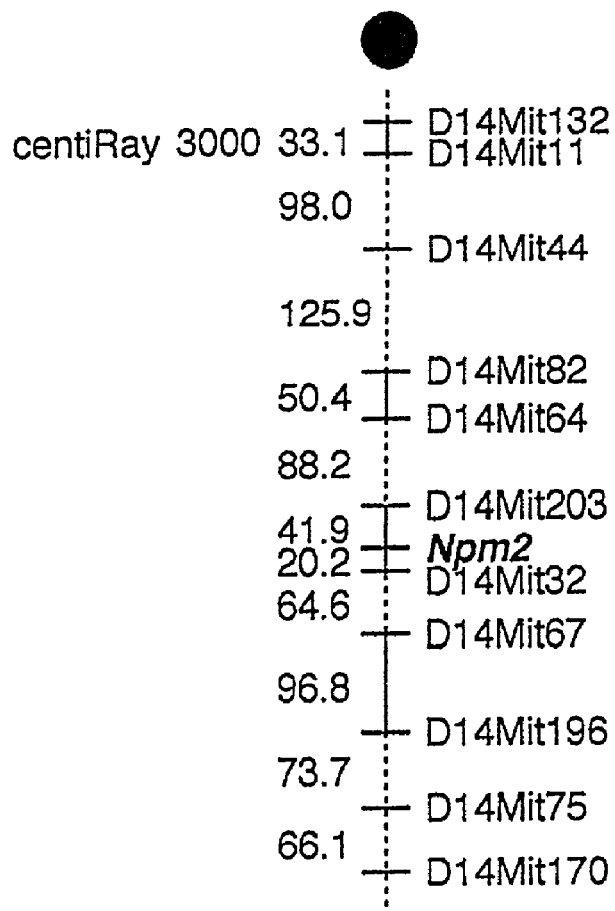
Haplotypes for T31 Chr 14 near Npm2
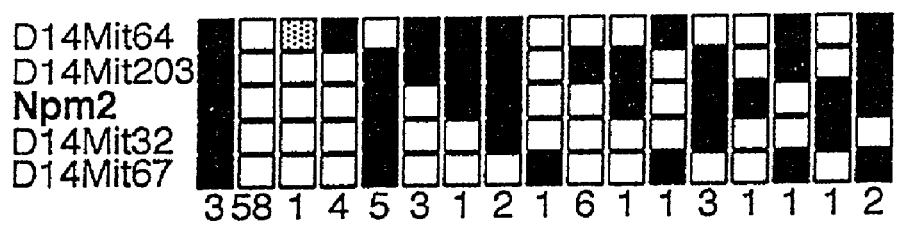
Figure 14

SEQUENCE LISTING

<160> NUMBER OF SEQ ID NOS: 15

<210> SEQ ID NO 1
<211> LENGTH: 1277
<212> TYPE: DNA
<213> ORGANISM: Mus musculus

<400> SEQUENCE: 1

```
aaggcgggcg aggcgcggga cgcacccatg ttcccggcga gcacgttcca cccctgcccg     60
catccttatc cgcaggccac caaagccggg gatggctgga ggttcggagc cagggggctgc    120
cgacccgcgc cccctccttt cctccccggc tacagacagc tcatggccgc ggagtacgtc    180
gacagccacc agcgggcaca gctcatggcc ctgctgtcgc ggatgggtcc ccggtcggtc    240
agcagccgtg acgctgcggt gcaggtgaac ccgcgccgcg acgcctcggt gcagtgttca    300
ctcgggcgcc gcacgctgca gcctgcaggg tgccgagcca gccccgacgc ccgatcgggt    360
tcctgtcaac cccgtggcca cgccggcgcc gggagatccc cgcgatcctg cagaccgta     420
gccccgttct cgtccgtgac cttctgtggc ctctcctcct cactggaggt tgcgggaggc    480
aggcagacac ccacgaaggg agaggggagc ccggcatcct cggggacccg ggaaccggag    540
ccgagagagg tggccgcgag gaaagcggtc ccccagccgc gaagcgagga gggcgatgtt    600
caggctgcag ggcaggccgg gtgggagcag cagccaccac cggaggaccg aacagtgtg     660
gcggcgatgc agtctgagcc tgggagcgag gagccatgtc ctgccgcaga gatggctcag    720
gaccccggtg attcggatgc ccctcgagac caggcctccc cgcaaagcac ggagcaggac    780
aaggagcgcc tgcgtttcca gttcttagag cagaagtacg gctactatca ctgcaaggac    840
tgcaaaatcc ggtgggagag cgcctatgtg tggtgtgtgc agggcaccag taaggtgtta    900
cttcaaacag ttctgccgag tgtgtgagaa atcctacaac ccttacagag tggaggacat    960
cacctgtcaa agttgtaaaa gaactagatg tgcctgccca gtcagatttc gccacgtgga   1020
ccctaaacgc ccccatcggc aagacttgtg tgggagatgc aaggacaaac gcctgtcctg   1080
cgacagcacc ttcagcttca aatacatcat ttagtgagag tcgaaaacgt ttctgctaga   1140
tggggctaat ggaatggaca agtgagcttt ctcccctctt cacctcttcc ctttccaaat   1200
tcttcatgac agacagtgtt acttggatat aaagcctgtg aataaaggt attgcaaaca    1260
aaaaaaaaaa aaaaaaa                                                 1277
```

<210> SEQ ID NO 2
<211> LENGTH: 361
<212> TYPE: PRT
<213> ORGANISM: Mus musculus

<400> SEQUENCE: 2

```
Met Phe Pro Ala Ser Thr Phe His Pro Cys Pro His Pro Tyr Pro Gln
1               5                   10                  15

Ala Thr Lys Ala Gly Asp Gly Trp Arg Phe Gly Ala Arg Gly Cys Arg
            20                  25                  30

Pro Ala Pro Pro Ser Phe Leu Pro Gly Tyr Arg Gln Leu Met Ala Ala
        35                  40                  45

Glu Tyr Val Asp Ser His Gln Arg Ala Gln Leu Met Ala Leu Leu Ser
    50                  55                  60

Arg Met Gly Pro Arg Ser Val Ser Ser Arg Asp Ala Ala Val Gln Val
65                  70                  75                  80
```

```
Asn Pro Arg Arg Asp Ala Ser Val Gln Cys Ser Leu Gly Arg Arg Thr
                85                  90                  95
Leu Gln Pro Ala Gly Cys Arg Ala Ser Pro Asp Ala Arg Ser Gly Ser
            100                 105                 110
Cys Gln Pro Arg Gly His Ala Gly Ala Gly Arg Ser Pro Arg Ser Trp
        115                 120                 125
Gln Thr Val Ala Pro Phe Ser Ser Val Thr Phe Cys Gly Leu Ser Ser
    130                 135                 140
Ser Leu Glu Val Ala Gly Gly Arg Gln Thr Pro Thr Lys Gly Glu Gly
145                 150                 155                 160
Ser Pro Ala Ser Ser Gly Thr Arg Glu Pro Glu Pro Arg Glu Val Ala
                165                 170                 175
Ala Arg Lys Ala Val Pro Gln Pro Arg Ser Glu Glu Gly Asp Val Gln
            180                 185                 190
Ala Ala Gly Gln Ala Gly Trp Glu Gln Gln Pro Pro Glu Asp Arg
        195                 200                 205
Asn Ser Val Ala Ala Met Gln Ser Glu Pro Gly Ser Glu Glu Pro Cys
    210                 215                 220
Pro Ala Ala Glu Met Ala Gln Asp Pro Gly Asp Ser Asp Ala Pro Arg
225                 230                 235                 240
Asp Gln Ala Ser Pro Gln Ser Thr Glu Gln Asp Lys Glu Arg Leu Arg
                245                 250                 255
Phe Gln Phe Leu Glu Gln Lys Tyr Gly Tyr Tyr His Cys Lys Asp Cys
            260                 265                 270
Lys Ile Arg Trp Glu Ser Ala Tyr Val Trp Cys Val Gln Gly Thr Ser
        275                 280                 285
Lys Val Tyr Phe Lys Gln Phe Cys Arg Val Cys Glu Lys Ser Tyr Asn
    290                 295                 300
Pro Tyr Arg Val Glu Asp Ile Thr Cys Gln Ser Cys Lys Arg Thr Arg
305                 310                 315                 320
Cys Ala Cys Pro Val Arg Phe Arg His Val Asp Pro Lys Arg Pro His
                325                 330                 335
Arg Gln Asp Leu Cys Gly Arg Cys Lys Asp Lys Arg Leu Ser Cys Asp
            340                 345                 350
Ser Thr Phe Ser Phe Lys Tyr Ile Ile
        355                 360

<210> SEQ ID NO 3
<211> LENGTH: 1817
<212> TYPE: DNA
<213> ORGANISM: Mus musculus

<400> SEQUENCE: 3
gtcacagctt tccctgccc gaatatggtg atctgtctcc attgtccaga tcaggatgat      60
tctttagaag aagtcacaga ggaatgctat tccccaccca ccctccagaa cctgcaatt    120
cagagtctac tgagggatga ggccttggcc atttctgctc tcacggacct gccccagagt   180
ctgttcccag taattttga ggaggccttc actgatggat atatagggat cttgaaggcc   240
atgataccctg tgtggcccctt cccatacctt tctttaggaa agcagataaa taattgcaac   300
ctggagactt tgaaggctat gcttgaggga ctagatatac tgcttgcaca aaaggttcaa   360
accagtaggt gcaaactcag agtaattaat tggagagaag atgacttgaa gatatgggct   420
ggatcccatg aaggtgaagg cttaccagat tcaggacag agaagcagcc aattgagaac   480
agtgctggct gtgaggtgaa gaaagaattg aaggtgacga ctgaagtcct tcgcatgaag   540
```

-continued

```
ggcagacttg atgaatctac cacatacttg ttgcagtggg cccagcagag aaaagattct     600
attcatctat tctgtagaaa gctactaatt gaaggcttaa ccaaagcctc agtgatagaa     660
atcttcaaaa ctgtacacgc agactgtata caggagctta tcctaagatg tatctgcata     720
gaagagttgg ctttcttaa tccctacctg aaactgatga aaagtctttt cacactcaca     780
ctagatcaca tcataggtac cttcagtttg ggtgattctg aaaagcttga tgaggagaca     840
atattcagct tgatttctca acttcccaca ctccactgtc tccagaaact ctatgtaaat     900
gatgtccctt ttataaaagg caacctgaaa gaatacctca ggtgcctgaa aaagcccttg     960
gagacacttt gcatcagtaa ctgtgacctc tcacagtcag acttggattg cctgccctat    1020
tgcctgaata tttgtgaact caaacatctg catattagtg atatatattt atgtgattta    1080
ctccttgagc ctcttggttt tctccttgag agagttggag ataccctgaa aaccctggaa    1140
ttggattcat gttgtatagt ggactttcag ttcagtgcct tgctgcctgc cctaagccaa    1200
tgttctcacc tcagagaggt cactttctat gataatgatg tttctctgcc tttcttgaaa    1260
acaacttcta caccacacag ccctgctgag tcagctgatc tatgagtgtt accctgcccc    1320
tctagagtgc tatgatgaca gtggtgtaat actaacacac agattagaaa gtttttgtcc    1380
tgagcttctg gatatactga gagccaaaag acagctccat agtgtctcct ttcaaacaac    1440
caaatgctct aaatgtggtg ggtgctacat ttatgatcgg catacccaat gttgccgttt    1500
tgtggaacta ctataagctt gattgtgaaa ctgagaaata gaaacttagt attggggact    1560
gatgaaatcc taagtgaatg tccactgcta aatggagcat gaaaatgtca atcacctaaa    1620
agtctgagat acacaggaaa gtcaataact tcctctgagc tggtgaatgg atgttgcatc    1680
tgtagaaagt atcaagcact tgtagtttga atgtgttaca atagaagcac catttatga    1740
gactggccca atctgttgac tgcatacaat aaatctgttg acttattaaa tttttaaaaa    1800
aaaaaaaaaa aaaaaaa                                                   1817
```

<210> SEQ ID NO 4
<211> LENGTH: 426
<212> TYPE: PRT
<213> ORGANISM: Mus musculus

<400> SEQUENCE: 4

```
Met Val Ile Cys Leu His Cys Pro Asp Gln Asp Ser Leu Glu Glu
1               5                   10                  15

Val Thr Glu Glu Cys Tyr Ser Pro Pro Thr Leu Gln Asn Leu Ala Ile
            20                  25                  30

Gln Ser Leu Leu Arg Asp Glu Ala Leu Ala Ile Ser Ala Leu Thr Asp
        35                  40                  45

Leu Pro Gln Ser Leu Phe Pro Val Ile Phe Glu Glu Ala Phe Thr Asp
    50                  55                  60

Gly Tyr Ile Gly Ile Leu Lys Ala Met Ile Pro Val Trp Pro Phe Pro
65                  70                  75                  80

Tyr Leu Ser Leu Gly Lys Gln Ile Asn Asn Cys Asn Leu Glu Thr Leu
                85                  90                  95

Lys Ala Met Leu Glu Gly Leu Asp Ile Leu Leu Ala Gln Lys Val Gln
            100                 105                 110

Thr Ser Arg Cys Lys Leu Arg Val Ile Asn Trp Arg Glu Asp Asp Leu
        115                 120                 125

Lys Ile Trp Ala Gly Ser His Glu Gly Glu Gly Leu Pro Asp Phe Arg
    130                 135                 140
```

-continued

```
Thr Glu Lys Gln Pro Ile Glu Asn Ser Ala Gly Cys Glu Val Lys Lys
145                 150                 155                 160
Glu Leu Lys Val Thr Thr Glu Val Leu Arg Met Lys Gly Arg Leu Asp
                165                 170                 175
Glu Ser Thr Thr Tyr Leu Leu Gln Trp Ala Gln Gln Arg Lys Asp Ser
            180                 185                 190
Ile His Leu Phe Cys Arg Lys Leu Leu Ile Glu Gly Leu Thr Lys Ala
        195                 200                 205
Ser Val Ile Glu Ile Phe Lys Thr Val His Ala Asp Cys Ile Gln Glu
    210                 215                 220
Leu Ile Leu Arg Cys Ile Cys Ile Glu Glu Leu Ala Phe Leu Asn Pro
225                 230                 235                 240
Tyr Leu Lys Leu Met Lys Ser Leu Phe Thr Leu Thr Leu Asp His Ile
                245                 250                 255
Ile Gly Thr Phe Ser Leu Gly Asp Ser Glu Lys Leu Asp Glu Glu Thr
            260                 265                 270
Ile Phe Ser Leu Ile Ser Gln Leu Pro Thr Leu His Cys Leu Gln Lys
        275                 280                 285
Leu Tyr Val Asn Asp Val Pro Phe Ile Lys Gly Asn Leu Lys Glu Tyr
    290                 295                 300
Leu Arg Cys Leu Lys Lys Pro Leu Glu Thr Leu Cys Ile Ser Asn Cys
305                 310                 315                 320
Asp Leu Ser Gln Ser Asp Leu Asp Cys Leu Pro Tyr Cys Leu Asn Ile
                325                 330                 335
Cys Glu Leu Lys His Leu His Ile Ser Asp Ile Tyr Leu Cys Asp Leu
            340                 345                 350
Leu Leu Glu Pro Leu Gly Phe Leu Leu Glu Arg Val Gly Asp Thr Leu
        355                 360                 365
Lys Thr Leu Glu Leu Asp Ser Cys Cys Ile Val Asp Phe Gln Phe Ser
370                 375                 380
Ala Leu Leu Pro Ala Leu Ser Gln Cys Ser His Leu Arg Glu Val Thr
385                 390                 395                 400
Phe Tyr Asp Asn Asp Val Ser Leu Pro Phe Leu Lys Thr Thr Ser Thr
                405                 410                 415
Pro His Ser Pro Ala Glu Ser Ala Asp Leu
            420                 425

<210> SEQ ID NO 5
<211> LENGTH: 1018
<212> TYPE: DNA
<213> ORGANISM: Mus musculus

<400> SEQUENCE: 5
gccatattga ggacctgcag tagaggtgga acccatgact ggcagcgcaa acacagtgat      60
aacagctgag ctccaagcaa ggacccagga ccttgcctca ccacagacat aatctttccc     120
cacaacacct ccaccaagcc gccctgtaaa tcgacatgag tcgccacagc accagcagcg     180
tgaccgaaac cacagcaaaa acatgctctg gggtagtga actcaatcag gaaaagcaga      240
cttgcacctt tagaggccaa ggcgagaaga aggacagctg taaactcttg ctcagcacga     300
tctgcctggg ggagaaagcc aaagaggagg tgaaccgtgt ggaagtcctc tcccaggaag     360
gcagaaaacc accaatcact attgctacgc tgaaggcatc agtcctgccc atggtcactg     420
tgtcaggtat agagctttct cctccagtaa cttttcggct caggactggc tcaggacctg     480
tgttcctcag tggcctggaa tgttatgaga cttcggacct gacctgggaa gatgacgagg     540
```

```
aagaggagga agaggaggag gaagaggatg aagatgagga tgcagatata tcgctagagg      600
agatacctgt caaacaagtc aaaagggtgg ctccccagaa gcagatgagc atagcaaaga      660
aaaagaaggt ggaaaagaa gaggatgaaa cagtagtgag gcccagccct caggacaaga       720
gtccctggaa gaaggagaaa tctacaccca gagcaaagac gccagtgacc aagaaatgac     780
ctcatcttag catcttctgc gtccaaggca ggatgtccag cagctgtgtt ttggtgcagg      840
tgtccagccc caccaccct gtctgaatgt aataaggtgg tgtggctgta accctgtaac      900
ccagccctcc agtttccgga ggttttggt gaagagcccc cagcaagttc gcctagggcc       960
acaataaaat ttgcatgatc aggaaaaaaa aaaaaaaaaa aaaaaaaaaa aaaaaaa       1018
```

<210> SEQ ID NO 6
<211> LENGTH: 207
<212> TYPE: PRT
<213> ORGANISM: Mus musculus

<400> SEQUENCE: 6

```
Met Ser Arg His Ser Thr Ser Ser Val Thr Glu Thr Thr Ala Lys Asn
1               5                   10                  15

Met Leu Trp Gly Ser Glu Leu Asn Gln Glu Lys Gln Thr Cys Thr Phe
            20                  25                  30

Arg Gly Gln Gly Glu Lys Lys Asp Ser Cys Lys Leu Leu Leu Ser Thr
        35                  40                  45

Ile Cys Leu Gly Glu Lys Ala Lys Glu Glu Val Asn Arg Val Glu Val
    50                  55                  60

Leu Ser Gln Glu Gly Arg Lys Pro Pro Ile Thr Ile Ala Thr Leu Lys
65                  70                  75                  80

Ala Ser Val Leu Pro Met Val Thr Val Ser Gly Ile Glu Leu Ser Pro
                85                  90                  95

Pro Val Thr Phe Arg Leu Arg Thr Gly Ser Gly Pro Val Phe Leu Ser
            100                 105                 110

Gly Leu Glu Cys Tyr Glu Thr Ser Asp Leu Thr Trp Glu Asp Asp Glu
        115                 120                 125

Glu Glu Glu Glu Glu Glu Glu Glu Asp Glu Asp Glu Asp Ala Asp
    130                 135                 140

Ile Ser Leu Glu Glu Ile Pro Val Lys Gln Val Lys Arg Val Ala Pro
145                 150                 155                 160

Gln Lys Gln Met Ser Ile Ala Lys Lys Lys Val Glu Lys Glu Glu
                165                 170                 175

Asp Glu Thr Val Val Arg Pro Ser Pro Gln Asp Lys Ser Pro Trp Lys
            180                 185                 190

Lys Glu Lys Ser Thr Pro Arg Ala Lys Lys Pro Val Thr Lys Lys
        195                 200                 205
```

<210> SEQ ID NO 7
<211> LENGTH: 214
<212> TYPE: DNA
<213> ORGANISM: Mus musculus

<400> SEQUENCE: 7

```
acagcagagg tgatgctcag aaatcaagtt ttaacagagg gccaggtgct tctagagtag       60
gaggggattg cacacctccc caccccctcc tctttcccag gcttcttaac agcctgctgt      120
gggaagctga cccttagatg gagccctgaa gccatattga ggacctgcag tagaggtgga      180
acccatgact ggcagcgcag taagcttgag cagg                                  214
```

<210> SEQ ID NO 8
<211> LENGTH: 194
<212> TYPE: DNA
<213> ORGANISM: Mus musculus

<400> SEQUENCE: 8

```
ctttgcatta ctcagaacac agtgataaca gctgagctcc aagcaaggac ccaggacctt      60
gcctcaccac agacataatc tttccccaca acacctccac caagccgccc tgtaaatcga     120
catgagtcgc cacagcacca gcagcgtgac cgaaaccaca gcaaaaaaca tgctctgggg     180
taagggctaa ggct                                                        194
```

<210> SEQ ID NO 9
<211> LENGTH: 116
<212> TYPE: DNA
<213> ORGANISM: Mus musculus

<400> SEQUENCE: 9

```
gtcttcgctg tgcaggtagt gaactcaatc aggaaaagca gacttgcacc tttagaggcc      60
aatgcgagaa gaaggacagc tgtaaactct tgctcagcac ggtgggtgtc tcccaa         116
```

<210> SEQ ID NO 10
<211> LENGTH: 144
<212> TYPE: DNA
<213> ORGANISM: Mus musculus

<400> SEQUENCE: 10

```
catcaccttt ctcagatctg cctgggggag aaagccaaag aggaggtgaa ccgtgtggaa      60
gtcctctccc aggaaggcag aaaaccacca atcactattg ctacgctgaa ggcatcagtc     120
ctgcccatgg tgagtcttct ctcc                                             144
```

<210> SEQ ID NO 11
<211> LENGTH: 124
<212> TYPE: DNA
<213> ORGANISM: Mus musculus

<400> SEQUENCE: 11

```
agaaggggga cacaggtcac tgtgtcaggt atagagcttt ctcctccagt aacttttcgg      60
ctcaggactg gctcaggacc tgtgttcctc agtggcctgg aatgttatgg taagttgtag     120
ccta                                                                   124
```

<210> SEQ ID NO 12
<211> LENGTH: 182
<212> TYPE: DNA
<213> ORGANISM: Mus musculus

<400> SEQUENCE: 12

```
ggctacccat tccagagact tcggacctga cctgggaaga tgacgaggaa gaggaggaag      60
aggaggagga agaggatgaa gatgaggatg cagatatatc gctagaggag atacctgtca     120
aacaagtcaa aagggtggct ccccagaagc agatgagcat agcaaaggtg gggggaaaag     180
aa                                                                     182
```

<210> SEQ ID NO 13
<211> LENGTH: 71
<212> TYPE: DNA
<213> ORGANISM: Mus musculus

```
<400> SEQUENCE: 13 tggttttgt tccagaaaaa gaaggtggaa aaagaagagg atgaaacagt agtgaggtaa      60
ttcatgcagt t                                                          71

<210> SEQ ID NO 14
<211> LENGTH: 64
<212> TYPE: DNA
<213> ORGANISM: Mus musculus

<400> SEQUENCE: 14
ctattccctt tccaggccca gccctcagga caagagtccc tggaagaagg tgagcaataa      60
gaag                                                                  64

<210> SEQ ID NO 15
<211> LENGTH: 364
<212> TYPE: DNA
<213> ORGANISM: Mus musculus

<400> SEQUENCE: 15
ctcttatctg cacaggagaa atctacaccc agagcaaaga agccagtgac caagaaatga      60
cctcatctta gcatcttctg cgtccaaggc aggatgtcca gcagctgtgt tctggtgcag     120
gtgtccagcc ccaccaccct agtctgaatg taataaggtg gtgtggctgt aaccctgtaa     180
cccagccctc cagtttccgg aggtttttgg tgaagagccc ccagcaagtt cgcctagggc     240
cacaataaaa tttgcatgat caggacctcc ctctgcctcc ccctccctgg atgggtctcc     300
tcgctgctgc gatagctcat gtgcccagca gagggcaacc acgagcaaga aaccagcccc     360
atgt                                                                 364
```

OVARY-SPECIFIC GENES AND PROTEINS

This application claims the benefit of U.S. Provisional Application No. 60/106,020 filed Oct. 28, 1999.

BACKGROUND OF THE INVENTION

1. Field of the Invention

The present invention relates generally to ovary-specific genes and the proteins they encode.

2. Description of Related Art

Reproductive development and function are complex processes involving both genetically-determined and physiological events. Identification of the critical protein products of genes involved in these processes is necessary to characterize how these processes are regulated. Although important molecular events occur during the early phases of mammalian oogenesis and folliculogenesis, to date, few "candidate" regulatory molecules have been identified and characterized thoroughly. Several studies have suggested that both endocrine factors, such luteinizing hormone (LH) and follicle stimulating hormone (FSH) from the pituitary, as well as paracrine factors secreted from the oocyte influence folliculogenesis. FSH and LH are known to bind to granulosa and thecal cells which in turn are required for oocyte growth and maturation and maintenance of oocyte meiotic competence. Likewise, oocytes may secrete factors which are necessary for normal granulosa cell and thecal cell function. Because oocyte growth is coordinated with the development and growth of the surrounding somatic cells (i.e., granulosa cells initially and thecal cells later), understanding the molecular events at early stages will give important clues about the paracrine factors mediating the reciprocal interactions between oocytes and somatic cells, the development of competence for trophic hormone stimulation, and the process of follicular recruitment.

Disruption of the hypothalamic-pituitary-gonadal reproductive axis by administration of steroids containing synthetic estrogens and progestins has been one of the oldest methods of hormonal contraception. However, the latest report of the Institute of Medicine emphasizes the importance of developing strategies for new contraceptives. According to the report, some of the long-term contraceptive strategies for women include inhibition of ovulation, prevention of fertilization, or blocking of implantation of a fertilized egg into the uterine lining. Furthermore, infertility affects ~15% of couples, and in ~40% of the cases, the female is believed to be the sole cause of the infertility. Thus, it is critical to identify novel ovary-specific gene products which could be potential targets for new contraceptive agents.

To identify key proteins in the hypothalamic-pituitary-gonadal axis, we have previously generated several important knockout mouse models, including four which have ovarian defects. Mice deficient in gonadal/pituitary peptide inhibin have secondary infertility due to the onset of ovarian or testicular tumors which appear as early as 4 weeks of age (Matzuk, et al., 1992). Mice deficient in activin receptor type II (ActRII) survive to adulthood but display reproductive defects. Male mice show reduced testes size and demonstrate delayed fertility (Matzuk, et al. 1995). In contrast, female mice have a block in folliculogenesis at the early antral follicle stage leading to infertility. Consistent with the known role of activins in FSH homeostasis, both pituitary and serum FSH levels are dramatically reduced in these ActRII knockout mice. Female mice deficient in FSH, due to a mutation in the FSHβ gene, are infertile (Kumar et al., 1997). However, these mice have an earlier block in folliculogenesis prior to antral follicle formation. Thus, FSH is not required for formation of a multi-layer pre-antral follicle, but it is required for progression to antral follicle formation. Finally, growth differentiation factor 9 (GDF-9)-deficient mice have been used to determine at which stage in follicular development GDF-9 is required (Dong et al., 1996). Expression of GDF-9 mRNA is limited to the oocyte and is seen at the early one-layer primary follicle stage and persists through ovulation. Absence of GDF-9 results in ovaries that fail to demonstrate any normal follicles beyond the primary follicle stage. Although oocytes surrounded by a single layer of granulosa cells are present and appear normal histologically, no normal two-layered follicles are present. Follicles beyond the one-layer stage are abnormal, contain atypical granulosa cells, and display asymmetric growth of these cells. Furthermore, as determined by light and electron microscopy, a thecal cell layer does not form in these GDF-9-deficient ovaries. Thus, in contrast to kit ligand and other growth factors which are synthesized by the somatic cells and influence oocyte growth, GDF-9 functions in the reciprocal manner as an oocyte-derived growth factor which is required for somatic cell function. The novel ovary-specific gene products presented herein are expected to function in similar ways to regulate oogenesis and/or somatic cell function (e.g., folliculogenesis).

SUMMARY OF THE INVENTION

The present invention provides three ovary-specific and oocyte-specific genes, O1-180, O1-184 and O1-236, the protein products they encode, fragments and derivatives thereof, and antibodies which are immunoreactive with these protein products. These genes and their protein products appear to relate to various cell proliferative or degenerative disorders, especially those involving ovarian tumors, such as germ cell tumors and granulosa cell tumors, or infertility, such as premature ovarian failure.

Thus, in one embodiment, the invention provides methods for detecting cell proliferative or degenerative disorders of ovarian origin and which are associated with O1-180, O1-184 or O1-236. In another embodiment, the invention provides method of treating cell proliferative or degenerative disorders associated with abnormal levels of expression of O1-180, O1-184 or O1-236, by suppressing or enhancing their respective activities.

The present invention provides key in vitro and in vivo reagents for studying ovarian development and function. The possible applications of these reagents are far-reaching, and are expected to range from use as tools in the study of development to therapeutic reagents against cancer. The major application of these novel ovarian gene products is to us them as reagents to evaluate potential contraceptives to block ovulation in women in a reversible manner. It will also be expected that these novel ovarian gene products will be useful to screen for genetic mutations in components of these signaling pathways that are associated with some forms of human infertility or gynecological cancers. In addition, depending on the phenotypes of humans with mutations in these genes or signaling pathways, we may consider using these novel ovarian gene products as reagent tools to generate a number of mutant mice for the further study of oogenesis and/or folliculogenesis. Such knockout mouse models will provide key insights into the roles of these gene products in human female reproduction and permit the use of these gene products as practical reagents for evaluation of new contraceptives.

BRIEF DESCRIPTION OF THE DRAWINGS

FIG. 1 shows the 1276 base pair cDNA sequence of gene O1-180 (SEQ ID NO: 1).

FIG. 2 shows the 361 amino acid sequence that is coded for by gene O1-180 (SEQ ID NO: 2).

FIG. 3 shows the 1817 base pair cDNA sequence of gene O1-184 (SEQ ID NO: 3).

FIG. 4 shows the 426 amino acid sequence that is coded for by gene O1-184 (SEQ ID NO: 4).

FIG. 5 shows the 1019 base pair cDNA sequence of gene O1-236 (SEQ ID NO: 5).

FIG. 6 shows the 207 amino acid sequence that is coded for by gene O1-236 (SEQ ID NO: 6)

FIG. 11) whereas the same codon of the 129SvEv gene is TGC (Cysteine; FIGS. 13A and 13B (SEQ ID NO: 7 through SEQ ID NO: 14)).

FIG. 11. Amino acid sequence conservation between mouse Npm2 and Xenopus laevis nucleoplasmin (Xnpm2). Using the NCB1 blast search tools, comparison of mouse Npm2 and Xnpm2 (accession # P05221) amino acid sequences reveals high identity (line connecting amino acids) and similarity (dots connecting amino acids). Spaces between the amino acids indicate gaps to aid in the alignment. Also identified are the conserved bipartite nuclear localization signal (bolded and underlined), the highly acidic "histone binding" region (boxed), and several conserved casein kinase II (CK2) and protein kinase C (PKC) phosphorylation sites (underlined and marked with "CK" or "PKC" with the serine or threonine in bold). Other predicted phosphorylation sites in either Npm2 or Xnpm2, which are not conserved, are not shown.

FIGS. 13A and 13B. Mouse Npm2 gene (SEQ ID NO: 7 through SEQ ID NO: 14) and amino acid sequences. Uppercase letters represent sequence identity with the Npm2 cDNA sequences; non-transcribed 5' and 3' sequences and intron sequences are shown in lowercase. The predicted transcription initiation codon, the termination codon, and the polyadenylation signal sequence are all underlined. Numbers along the left side represent the amino acids. The underlined and bolded "T" in codon 36, the bolded "c" for amino acid 26, and the underlined and bolded "C: in the 3' UTR sequence indicate differences between the cDNA and gene sequences. Arrows indicate where the O1-236 fragment initiates and ends in the cDNA sequence.

FIG. 14. Chromosomal localization of the mouse Npm2 gene. (Top) Map figure from the T31 radiation hybrid database at The Jackson Laboratory showing Chromosome 14 data. The map is depicted with the centromere toward the top. Distances between adjacent loci in centiRay3000 are shown to the left of the chromosome bar. The positions of some of the chromosome 14 MIT markers are shown on the right. Npm2 is positioned between D14Mit203 and D14Mit32. Missing typings were inferred from surrounding data where assignment was unambiguous. Raw data from The Jackson Laboratory were obtained from the Wold Wide Web address http://wwwjax.org/resources/documents/cm-data/rhmap/rh.html. (Bottom) Haplotype figure from the T31 radiation hybrid database at The Jackson Laboratory showing part of Chromosome 14 with loci linked to Npm2. Loci are listed in the best fit order with the most proximal at the top. The black boxes represent hybrid cell lines scoring positive for the mouse fragment and the white boxes represent cell lines scoring as negative. The grey box indicates an untyped or ambiguous line. The number of lines with each haplotype is given at the bottom of each column of boxes. Missing typings were inferred from surrounding data where assignment was unambiguous.

DETAILED DESCRIPTION OF THE INVENTION

Figure 7:
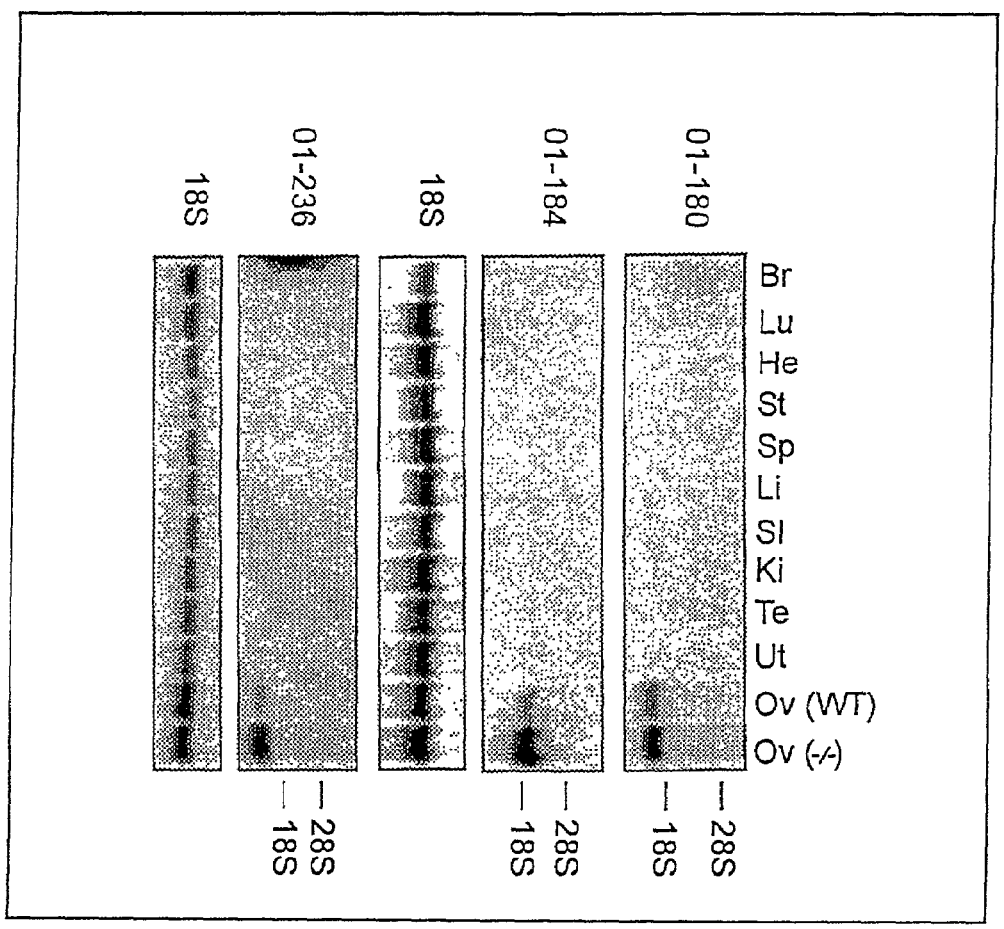
FIG. 7. Multi-tissue Northern blot analysis of ovary-specific genes. Northern blot analysis was performed on total RNA using O1-180, O1-184, and O1-236 probes. These gene products demonstrate an ovary-specific pattern (OV, ovary; WT, wild-type; -/-, GDF-9-deficient) as shown. The migration positions of 18S and 28S ribosomal RNA are indicated. All lanes had approximately equal loading as demonstrated using an 118S rRNA cDNA probe. Br, brain; Lu, lung; He, heart; St, stomach; Sp, spleen; Li, liver; SI, small intestine; Ki, kidney; Te, testes; Ut, uterus.

The present invention provides three novel proteins, O1-180, O1-184, O1-236, the polynucleotide sequences that encode them, and fragments and derivatives thereof. Expression of O1-180, O1-184, O1-236 is highly tissue-specific, being expressed in cells primarily in ovarian tissue. In one embodiment, the invention provides a method for detection of a cell proliferative or degenerative disorder of the ovary, which is associated with expression of O1-180, O1-184 or O1-236. In another embodiment, the invention provides a method for treating a cell proliferative or degenerative disorder associated with abnormal expression of O1-180, O1-184, O1-236 by using an agent which suppresses or enhances their respective activities.

Based on the known activities of many other ovary specific proteins, it can be expected that O1-180, O1-184 and O1-236, as well as fragments and derivatives thereof, will also possess biological activities that will make them useful as diagnostic and therapeutic reagents.

For example, GDF-9 is an oocyte-expressed gene product which has a similar pattern of expression as O1-180, O1-184, and O1-236. We have shown that mice lacking GDF-9 are infertile at a very early stage of follicular development, at the one-layer primary follicle stage (Dong, et al.). These studies demonstrate that agents which block GDF-9 function would be useful as contraceptive agents in human females. Since O1-180, O1-184, and O1-236 have an expression pattern in the oocyte (FIG. 8) which is nearly identical to GDF-9, this suggests that mice and humans or any other mammal lacking any of all of these gene products would also be infertile. Thus, blocking the function of any or all of these gene products would result in a contraceptive action.

Another regulatory protein that has been found to have ovary-specific expression is inhibin, a specific and potent polypeptide inhibitor of the pituitary secretion of FSH. Inhibin has been isolated from ovarian follicular fluid. Because of its suppression of FSH, inhibin has been advanced as a potential contraceptive in both males and females. O1-180, O1-184 and O1-236 may possess similar biological activity since they are also ovarian specific peptides. Inhibin has also been shown to be useful as a marker for certain ovarian tumors (Lappohn, et al., *N. Engl. J. Med.*, 321:790, 1989). O1-180, O1-184, O1-236 may also be useful as markers for identifying primary and metastatic neoplasms of ovarian origin. Likewise, mice which lack inhibin develop granulosa cell tumors (Matzuk et al., 1992). Similarly, O1-180, O1-184 and O1-236 may be useful as indicators of developmental anomalies in prenatal screening procedures.

Mullerian inhibiting substance (MIS) peptide, which is produced by the testis and is responsible for the regression of the Mullerian ducts in the male embryo, has been shown to inhibit the growth of human ovarian cancer in nude mice (Donahoe, et al., *Ann. Surg.*, 194:472, 1981). O1-180, O1-184 and O1-236 may function similarly and may, therefore, be targets for anti-cancer agents, such as for the treatment of ovarian cancer.

O1-180, O1-184 and O1-236, and agonists and antagonists thereof can be used to identify agents which inhibit fertility (e.g., act as a contraceptive) in a mammal (e.g., human). Additionally, O1-180, O1-184 and O1-236 and agonists and antagonists thereof can be used to identify agents which enhance fertility (e.g., increase the success of in vivo or in vitro fertilization) in a mammal. Likewise, assays of these or related oocyte-expressed gene products can be used in diagnostic assays for detecting forms of infertility (e.g., in an assay to analyze activity of these gene products) or other diseases (e.g., germ cell tumors, polycystic ovary syndrome).

O1-180, O1-184 and O1-236 or agents which act on these pathways may also function as growth stimulatory factors and, therefore, be useful for the survival of various cell populations in vitro. In particular, if O1-180, O1-184 and/or O1-236 play a role in oocyte maturation, they may be useful targets for in vitro fertilization procedures, e.g., in enhancing the success rate.

The term "substantially pure" as used herein refers to O1-180, O1-184 and O1-236 which are substantially free of other proteins, lipids, carbohydrates or other materials with which they are naturally associated. One skilled in the art can purify O1-180, O1-184 and O1-236 using standard techniques for protein purification. The substantially pure polypeptide will yield a single major band on a non-reducing polyacrylamide gel. The purity of the O1-180, O1-184 and O1-236 polypeptides can also be determined by amino-terminal amino acid sequence analysis. O1-180, O1-184 and O1-236 polypeptides includes functional fragments of the polypeptides, as long as their activities remain. Smaller peptides containing the biological activities of O1-180, O1-184 and O1-236 are included in the invention.

The invention provides polynucleotides encoding the O1-180, O1-184 and O1-236 proteins and fragments and derivatives thereof. These polynucleotides include DNA, cDNA and RNA sequences which encode O1-180, O1-184 or O1-236. It is understood that all polynucleotides encoding all or a portion of O1-180, O1-184 and/or O1-236 are also included herein, as long as they encode a polypeptide with the activity of O1-180, O1-184 or O1-236. Such polynucleotides include naturally occurring, synthetic, and intentionally manipulated polynucleotides. For example, polynucleotides of O1-180, O1-184 or O1-236 may be subjected to site-directed mutagenesis. The polynucleotide sequences for O1-180, O1-184 and O1-236 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequences of O1-180, O1-184 and O1-236 polypeptides encoded by the nucleotide sequences are functionally unchanged.

Minor modifications of the recombinant O1-180, O1-184 and O1-236 primary amino acid sequences may result in proteins which have substantially equivalent activity as compared to the respective O1-180, O1-184 and O1-236 polypeptides described herein. Such modifications may be deliberate, as by site-directed mutagenesis, or may be spontaneous. All of the polypeptides produced by these modifications are included herein as long as the biological activity of O1-180, O1-184 or O1-236 still exists. Further, deletion of one or more amino adds can also result in a modification of the structure of the resultant molecule without significantly altering its biological activity. This can lead to the development of a smaller active molecule which would have broader utility. For example, one could remove amino or carboxy terminal amino acids which may not be required for biological activity of O1-180, O1-184 or O1-236.

The nucleotide sequences encoding the O1-180, O1-184 and O1-236 polypeptides of the invention include the disclosed sequences and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

For the purpose of this invention, the term "derivative" shall mean any molecules which are within the skill of the ordinary practitioner to make and use, which are made by derivatizing the subject compound, and which do not destroy the activity of the derivatized compound. Compounds which meet the foregoing criteria which diminish, but do not destroy, the activity of the derivatized compound are considered to be within the scope of the term "derivative." Thus, according to the invention, a derivative of a compound comprising amino acids in a sequence corresponding to the sequence of O1-180, O1-184 or O1-236, need not comprise a sequence of amino acids that corresponds exactly to the sequence of O1-180, O1-184 or O1-236, so long as it retains a measurable amount of the activity of the O1-180, O1-184 or O1-236.

Fragments of proteins are seen to include any peptide that contains 6 contiguous amino acids or more that are identical to 6 contiguous amino acids of either of the sequences shown in FIGS. 2 (SEQ ID NO: 2), 4 (SEQ ID NO: 4), 6 (SEQ ID NO: 6), 11 and 14. Fragments that contain 7, 8, 9, 10, 11, 12, 13, 14 and 15 or more contiguous amino acids or more that are identical to a corresponding number of amino acids of any of the sequences shown in FIGS. 2 (SEQ ID NO: 2), 4 (SEQ ID NO: 4), 6 (SEQ ID NO: 6), 11 and 14 are also contemplated. Fragments may be used to generate antibodies. Particularly useful fragments will be those that make up domains of O1-180, O1-184 or O1-236. Domains are defined as portions of the proteins having a discrete tertiary structure and that is maintained in the absence of the remainder of the protein. Such structures can be found by techniques known to those skilled in the art. The protein is partially digested with a protease such as subtilisin, trypsin, chymotrypsin or the like and then subjected to polyacrylamide gel electrophoresis to separate the protein fragments. The fragments can then be transferred to a PVDF membrane and subjected to micro sequencing to determine the amino acid sequence of the N-terminal of the fragments.

DNA sequences of the invention can be obtained by several methods. For example, the DNA can be isolated using hybridization or amplification techniques which are well known in the art. These include, but are not limited to: 1) hybridization of genomic or cDNA libraries with probes to detect homologous nucleotide sequences, 2) antibody screening of expression libraries to detect cloned DNA fragments with shared structural features, or 3) use of oligonucleotides related to these sequences and the technique of the polymerase chain reaction.

Preferably the O1-180, O1-184 and O1-236 polynucleotides of the invention are derived from a mammalian organism, and most preferably from a mouse, rat, pig, cow or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA done by the hybridization of the target DNA to that single probe in the mixture which is its complete complement (Wallace, et al., *Nucl. Acid Res.,* 9:879, 1981).

The development of specific DNA sequences encoding O1-180, O1-184 and O1-236 can also be obtained by: 1) isolation of double-stranded DNA sequences from the genomic DNA; 2) chemical manufacture of a DNA sequence to provide the necessary codons for the polypeptides of interest; and 3) in vitro synthesis of a double stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptides is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for O1-180, O1-184 and/or O1-236 peptides having at least one epitope, using antibodies specific for O1-180, O1-184 and/or O1-236. Such antibodies can be either polyclonally or monoclonally derived and used to detect expression product indicative of the presence of O1-180, O1-184 and/or O1-236 cDNA.

DNA sequences encoding O1-180, O1-184 or O1-236 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the O1-180, O1-184 and/or O1-236 polynucleotide sequences may be inserted into a recombinant expression vector. The term "recombinant expression vectors" refers to a plasmid, virus or other vehicle known in the art that has been manipulated by insertion or incorporation of the O1-180, O1-184 or O1-236 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein 1, or polyhedrin promoters). Polynucleotide sequences encoding O1-180, O1-184 or O1-236 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transformed with DNA sequences encoding the O1-180, O1-184 or O1-236 cDNA sequences of the invention, and a second foreign DNA molecule encoding a selectable phenotype, such as the neomycin resistance gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with O1-180, O1-184 or O1-236 polypeptides or functional fragments thereof. Antibody which consists essentially of pooled monoclonal antibodies with different epitopic specificities, as well as distinct monoclonal antibody preparatory are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and F(ab')2, which are capable of binding an epitopic determinant on O1-180, O1-184 or O1-236.

The term "cell-proliferative disorder" denotes malignant as well as non-malignant cell populations which often appear to differ from the surrounding tissue both morphologically and genotypically. The O1-180, O1-184 and O1-236 polynucleotides that are antisense molecules are useful in treating malignancies of the various organ systems, particularly, for example, the ovaries. Essentially, any disorder which is etiologically linked to altered expression of O1-180, O1-184 or O1-236 could be considered susceptible to treatment with a O1-180, O1-184 or O1-236 suppressing reagent, respectively.

The invention provides a method for detecting a cell proliferative disorder of the ovary which comprises contacting an anti-O1-180, O1-184 or O1-236 antibody with a cell suspected of having an O1-180, O1-184 or O1-236 associated disorder and detecting binding to the antibody. The antibody reactive with O1-180, O1-184 or O1-236 is labeled with a compound which allows detection of binding to O1-180, O1-184 or O1-236, respectively. For purposes of the invention, an antibody specific for an O1-180, O1-184 or O1-236 polypeptide may be used to detect the level of O1-180, O1-184 or O1-236, respectively, in biological fluids and tissues. Any specimen containing a detectable amount of antigen can be used. A preferred sample of this invention is tissue of ovarian origin, specifically tissue containing oocytes or ovarian follicular fluid. The level of O1-180, O1-184 or O1-236 in the suspect cell can be compared with the level in a normal cell to determine whether the subject has an O1-180, O1-184 or O1-236-associated cell proliferative disorder. Preferably the subject is human. The antibodies of the invention can be used in any subject in which it is desirable to administer in vitro or in vivo immunodiagnosis or immunotherapy. The antibodies of the invention are suited for use, for example, in immuno assays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (ELISA) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "cell-degenerative disorder" denotes the loss of any type of cell in the ovary, either directly or indirectly. For example, in the absence of GDF-9, there is a block in the growth of the granulosa cells leading to eventual degeneration (i.e., death) of the oocytes (Dong et al., 1996). This death of the oocyte appears to lead to differentiation of the granulosa cells. In addition, in the absence of GDF-9, no normal thecal cell layer is formed around the follicles. Thus, in the absence of one oocyte-specific protein, GDF-9, there are defects in three different cell lineages, oocytes, granulosa cells, and thecal cells. In a similar way, death or differentiation of these various cell lineages could be affected by absence or misexpression of O1-180, O1-184, or O1-236. Furthermore, absence or misexpression of O1-180, O1-184, or O1-236 could result in defects in the oocyte/egg leading to the inability of the egg to be fertilized by spermatozoa.

The antibodies of the invention can be bound to many different carriers and used to detect the presence of an antigen comprising the polypeptide of the invention. Samples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen composing a polypeptide of the invention for which the monoclonal antibodies are specific. The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio. As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Ti.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{55}$Cr and $^{56}$Fe.

The monoclonal antibodies of the invention can be used in vitro and in vivo to monitor the course of amelioration of an O1-180, O1-184 or O1-236-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the O1-180, O1-184 or O1-236-associated disease is effective. The term "ameliorate" denotes a lessening of the detrimental effect of the O1-180, O1-184 or O1-236-associated disease in the subject receiving therapy.

The present invention identifies nucleotide sequences that can be expressed in an altered manner as compared to expression in a normal cell, therefore, it is possible to design appropriate therapeutic or diagnostic techniques directed to this sequence. Thus, where a cell-proliferative disorder is associated with the expression of O1-180, O1-184 or O1-236, nucleic acid sequences that interfere with the expression of O1-180, O1-184 or O1-236, respectively, at the translational level can be used. This approach utilizes, for example, antisense nucleic acids or ribozymes to block translation of a specific O1-180, O1-184 or O1-236 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target O1-180, O1-184 or O1-236-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or degenerative disorders which are mediated by O1-180, O1-184 or O1-236 proteins. Such therapy would achieve its therapeutic effect by introduction of the respective O1-180, O1-184 or O1-236 cDNAs or O1-180, O1-184, or O1-236 antisense polynucleotide into cells having the proliferative or degenerative disorder. Delivery of O1-180, O1-184, or O1-236 cDNAs or antisense O1-180, O1-184 or O1-236 polynucleotides can be achieved using a recombinant expression vector such as a chimeric virus or a colloidal dispersion system.

Especially preferred for therapeutic delivery of cDNAs or antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting an O1-180, O1-184 or O1-236 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector.

Those of skill in the art will know of, or can readily ascertain without undue experimentation, specific polynucleotide sequences which can be inserted into the retroviral genome to allow target specific delivery of the retroviral vector containing a O1-180, O1-184 or O1-236 cDNA or O1-180, O1-184, or O1-236 antisense polynucleotides.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packing mechanism to recognize an RNA transcript for encapsidation. Helper cell lines which ave deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for O1-180, O1-184 or O1-236 cDNAs or O1-180, O1-184, or O1-236 antisense polynucleotides is a colloidal dispersion system. Colloidal dispersion systems include macromolecule complexes, nanocapsules complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high exigency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Manning, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of O1-180, O1-184 and O1-236 in the reproductive tract, there are a variety of applications using the polypeptides, polynucleotides and antibodies of the invention, related to contraception, fertility and pregnancy. O1-180, O1-184 and O1-236 could play a role in regulation of the menstrual cycle and, therefore, could be useul in various contraceptive regimens.

The following examples are intended to illustrate but not limit the invention. While they are typical of those that might be used, other procedures known to those skilled in the art may alternatively be used.

EXAMPLE 1

Creation of a cDNA Subtractive Hybridization Library

Ovaries from GDF-9-deficient mice are histologically very different from wild-type ovaries due to the early block in folliculogenesis. In particular, one layer primary follicles are relatively enriched in GDF-9-deficient ovaries and abnormal follicular nests are formed after oocyte loss. We took advantage of these differences in ovary composition and related them to alterations in gene expression patterns to clone novel ovary-expressed transcripts which are upregulated in the GDF-9-deficient ovaries.

Ovaries from either GDF-9-deficient mice (C57BL/6/129SvEv hybrid) or wild-type mice were collected and polyA+ mRNA was made from each pool. Using a modified version of the CLONTECH PCR-Select Subtraction kit, we generated a pBluescript SK+plasmid-based cDNA library which was expected to be enriched for sequences upregulated in the GDF-9-deficient ovaries. Ligations into the NotI site of pBluescript SK+ were performed with a low molar ratio of EagI-digested cDNA fragment inserts to vector to prevent multiple inserts into the vector. Transformations were performed, and >1000 independent bacterial clones were picked and stored in glycerol at −80° C. The remainder of the ligation mix was stored at −80° C. for future transformations.

EXAMPLE 2

Initial Sequence Analysis of pOvary1 (pO1) Library Inserts

We performed sequence analysis of 331 inserts from the pO1 subtractive hybridization of cDNA library. An Applied Biosystems 373 DNA Sequencer was used to sequence these clones. BLAST searches were performed using the National Center for Biotechnology Information databases. Novel sequences were analyzed for open reading frames and compared to previously identified novel sequences using DNASTAR analysis programs. A summary of the data is presented in Table 1. As shown, the majority of the clones were known genes or match mouse or human ESTs. 9.4% of the clones fail to match any known sequence in the database.

EXAMPLE 3

Expression Analysis and cDNA Screening of Ovarian-Expressed Genes with No Known Function The functions of the pO1-library gene products which match ESTs or where there is no match are not known (Table 1). Northern blot analysis was performed on all cDNAs which failed to match sequences in any database. Additionally, sequences matching ESTs derived predominantly from mouse 2-cell embryo cDNA libraries (e.g., O1-91, O1-184, and O1-236) were analyzed. The rationale for analyzing this last group of ESTs is that mRNAs expressed at high levels in oocytes may persist until the 2-cell stage and may play a role in early embryonic development including fertilization of the egg or fusion of the male and female pronuclei.

Figure 8:
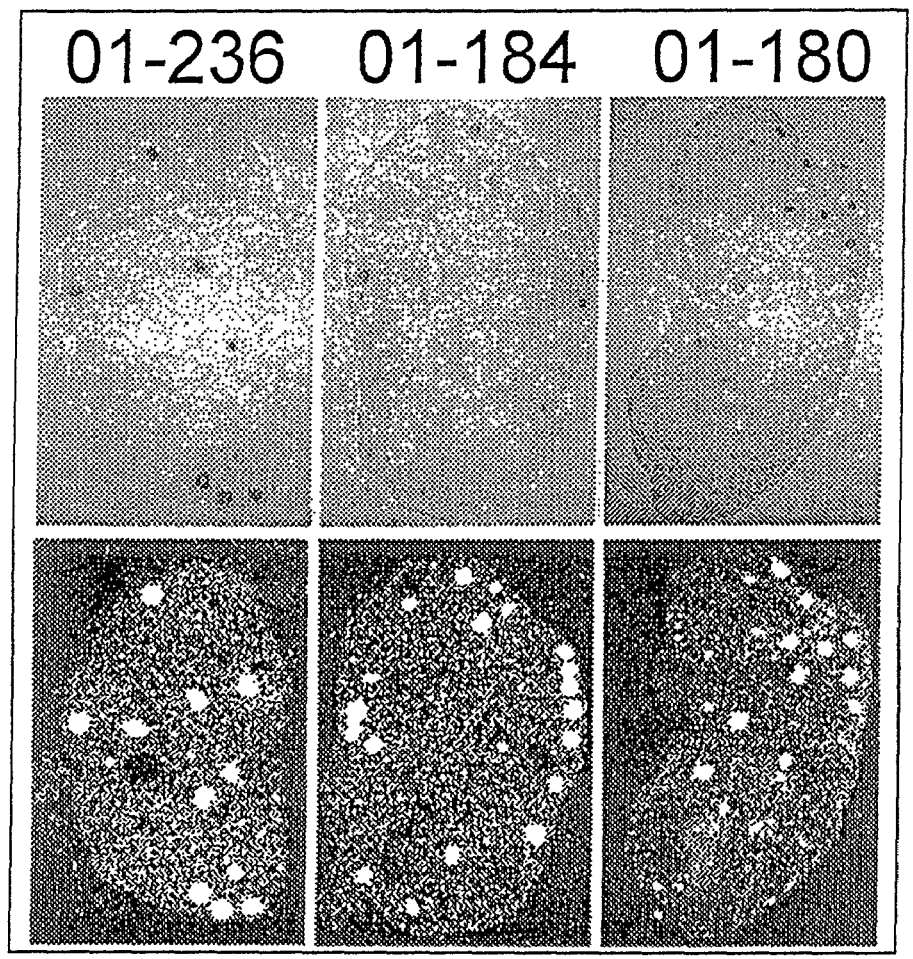
FIG. 8. In situ hybridization analysis of ovary-specific genes in mouse ovaries. In situ hybridization was performed using anti-sense probes to O1-180 (A, B), O1-184 (C,D) and O1-236 (E,F). A, C, and E are brightfield analysis of the ovaries. B, D, and F are darkfield analysis of the same ovary sections. All genes demonstrate specific expression in the oocyte beginning at the one layer primary follicle stage (small arrows) and continuing through the antral follicle stage (large arows). The "sense" probe does not detect a signal for any of these three ovary-specific genes (data not shown).

The results of the initial screen of novel ovarian genes is presented in Table 2. Northern blot analysis of 23 clones demonstrated that 8 of these clones were upregulated in the GDF-9-deficient ovary indicating the subtractive hybridization protocol used was adequate. Northern blot analysis using total RNA isolated from either adult C57BL/6/129SvEv hybrid mice (the ovarian RNA) or Swiss WEBSTER mice (all other tissues) also demonstrated that four of these clones including 2 clones which matched ESTs sequenced from 2-cell libraries were only expressed in the ovary (FIG. 7). The O1-236 fragment probe (749 bp) detected a transcript of approximately 1.0 kb (FIG. 7). Several clones have so far been analyzed for their ovarian localization by in situ hybridization analysis (FIG. 8). Clones O1-180, O1-184, and O1-236 were oocyte-specific and expressed in oocytes of primary (one-layer) preantral follicles through ovulation (FIG. 8).

Figure 9:
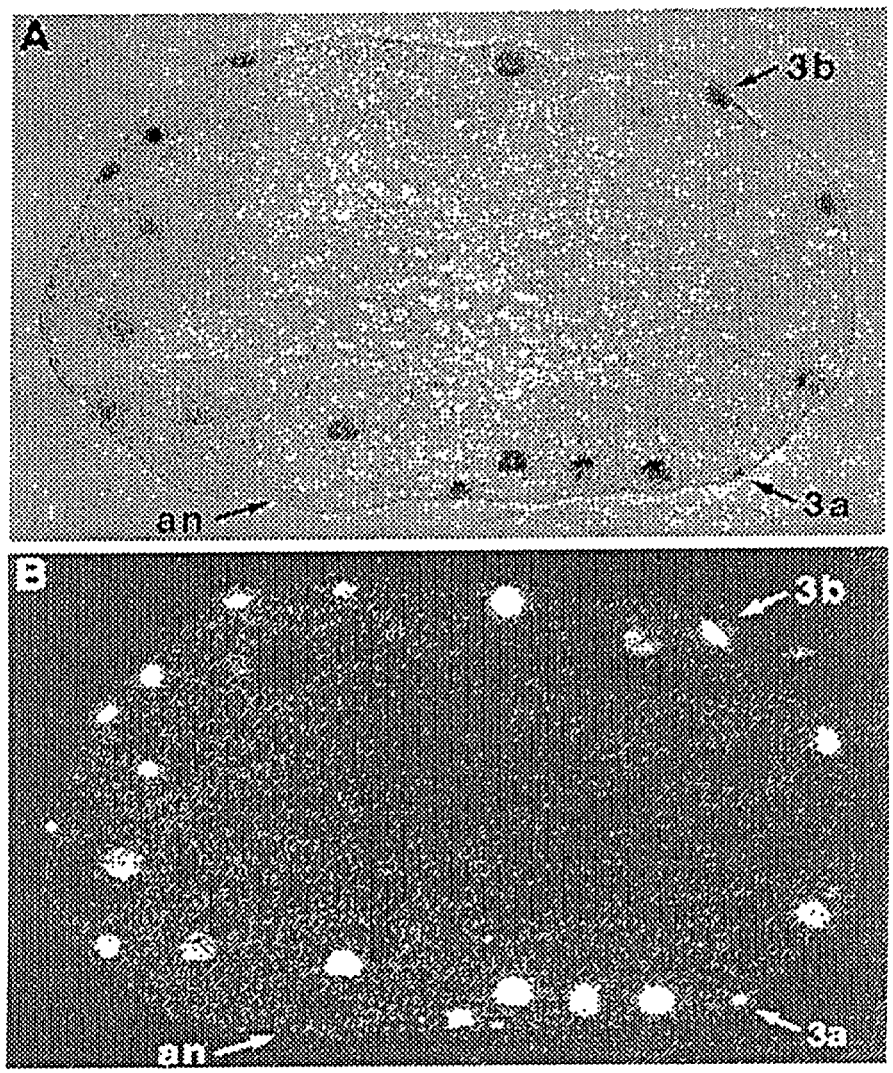
FIG. 9. In situ hybridization analysis of O1-236 in mouse ovaries. In situ hybridization was performed using probe O1-236 (partial Npm2 fragment). Brightfield analysis (A) and darkfield analysis (B) of the O1-236 mRNA in the same adult ovary sections. The probe demonstrates specific expression in all growing oocytes. Oocyte-specific expression is first seen in the early one layer primary follicle (type 3a), with higher expression in the one layer type 3b follicle and all subsequent stages including antral (an) follicles. The "sense" probe does not detect a signal for this oocyte-specific gene (data not shown).

The O1-236 gene product is oocyte-specific (FIG. 9). O1-236 is not expressed in oocytes of primordial (type 2) or small type 3a follicles (Pedersen et al., *Journal of Reproduction and Fertility*, 17:555-557, 1968) (data not shown) but is first detected in oocytes of intermediate-size type 3a follicles and all type 3b follicles (i.e., follicles with >20 granulosa cells surrounding the oocyte in largest cross-section). Expression of the O1-236 mRNA persisted through the antral follicle stage. Interestingly, the oocyte-specific expression pattern of the O1-236 gene product parallels the expression of other oocyte-specific genes which we have studied including Gdf9 (McGrath et al., *Molecular Endocrinology* 9:131-136 (1995)) and bone morphogenetic protein 15 (Dube et al., *Molecular Endocrinology* 12:1809-1817, 1998).

EXAMPLE 4

Cloning of Ovary Specific Genes, Including Mouse Npm2 the Mammalian Ortholog of *Xenopus laevis* Nucleoplasmin (Xnpm2)

Wild-type ovary and GDF-9-deficient ZAP Express ovary cDNA libraries were synthesized and were screened to isolate full-length cDNAs for the above-mentioned three clones. Each full-length cDNA was again subjected to database searches and analyzed for an open reading frame, initiation ATG, and protein homology. The full-length cDNAs approximate the mRNA sizes determined from Northern blot analysis.

Database searches using the predicted amino acid sequence permitted the identification of important domains (e.g., signal peptide sequences, transmembrane domains, zinc fingers, etc.) which will be useful to define the possible function and cellular localization of the novel protein.

The O1-236 partial cDNA fragment identified in Example 1 was used to screen Matzuk laboratory ZAP Express (Stratagene) ovarian cDNA libraries generated from either wild-type or GDF-9 deficient ovaries as per manufacturer's instructions and as described previously (Dube, et al., *Molecular Endocrinology*, 12:1809-1817 (1998)). In brief, approximately 300,000 clones of either wild-type or GDF-9 knockout mouse ovary cDNA libraries were hybridized to

[α-$^{32}$P] dCTP random-primed probes in Church's solution at 63° C. Filters were washed with 0.1× Church's solution and exposed overnight at −80° C.

Figure 10:
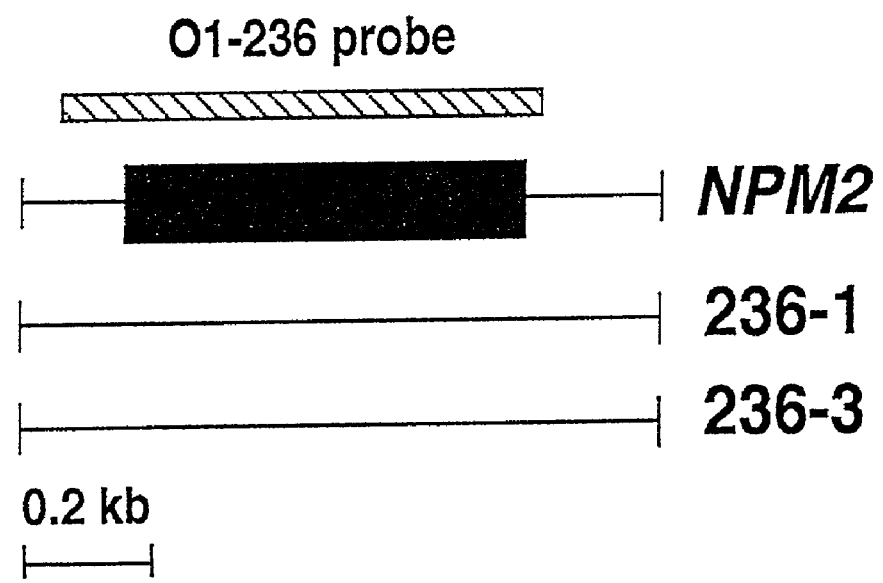
FIG. 10. Npm2 cDNA representation. Schematic representation of the mouse Npm2 cDNA sequence (984 bp) and two of the clones isolated from the mouse ovary CDNA libraries. The original O1-236 probe (749 bp) is shown at the top and encompasses the entire Npm2 open reading frame. The open reading frame (solid box) is 621 bp and the 5' UTR and 3' UTR sequences (thin lines) are 155 bp and 205 bp, respectively. The polyA sequences are not depicted. Clone 236-1 was isolated from the wild-type ovary cDNA library and clone 236-3 was isolated from the GDF-9-deficient ovary cDNA library. Clone 236-3 (984 bp excluding polyA sequence) is 4 bp longer at the 5' end and 1 bp longer at the 3' end than clone 236-1 (979 bp excluding polyA sequences). Codon 36 of the open reading frame of both cDNAs is GGC (Glycine.

Upon primary screening of the mouse ovarian cDNA libraries, the O1-236 cDNA fragment detected 22 positive phage clones out of 300,000 screened. Two of these clones (236-1 and 236-3), which approximated the mRNA size and which were derived from the two independent libraries, were analyzed further by restriction endonuclease digestion and DNA sequence analysis. These independent clones form a 984 bp overlapping contig (excluding the polyA sequences) and encode a 207 amino acid open reading frame (FIG. 10). Including the polyA tail, this sequence approximates the 1.0 kb mRNA seen by Northern blot analysis suggesting that nearly all of the 5' UTR sequence has been isolated. When the nucleotide sequence is subjected to public database search, no significant matches were derived. However, database search with the 207 amino acid open reading frame demonstrated high homology with several nucleoplasmin homologs from several species. Interestingly, O1-236 shows highest homology with Xenopus laevis nucleoplasmin. At the amino acid level, O1-236 is 48% identical and 71% similar to Xenopus laevis nucleoplasmin (FIG. 11). Based on this homology and the expression patterns of both gene products in oocytes, we have termed our gene Npm2 since it is the mammalian ortholog of Xenopus laevis nucleoplasmin [called Xnpm2 in (MacArthur et al., Genomics rs: 137-140 (1997))].

When the Npm2 and nucleoplasmin sequences are compared, several interesting features are realized. Nucleoplasmin has a bipartite nuclear localization signal consisting of KR-(X)$_{10}$-KKKK (Dingwall, et al. EMBO J. 6:69-74 (1987)). Deletion of either of these basic amino acid clusters in nucleoplasmin prevents translocation to the nucleus (Robbins et al. Cell 64:615-623 (1991)). When the Npm2 sequence is analyzed, this bipartite sequence is 100% conserved between the two proteins (FIG. 11). Thus, Npm2 would be predicated to translocate to the nucleus where it would primarily function.

Also conserved between Npm2 and nucleplasmin is a long stretch of negatively charged residues. Amino acids 125–144 of Npm2 and amino acids 128–146 of nucleoplasmin are mostly glutamic acid and aspartic acid residues, with 19 out of the 20 residues for Npm2 and 16 out of the 19 residues for nucleoplasmin either Asp or Glu. This region of Xenopus laevis nucleoplasmin has been implicated to bind the positively charged protamines and histones. Thus, a similar function for this acidic region of Npm2 is predicted.

The last obvious feature of the Npm2 and nucleoplasmin sequences is the high number of serine and threonine residues. The Npm2 sequence contains 19 serine and 17 threonines (i.e., 17.2% of the residues) and nucleoplasmin has 12 serine and 11 threonine residues (i.e., 11.5% of the residues). Multiple putative phosphorylation sites are predicted from the Npm2 and nucleoplasmin sequences. Several putative phosphorylation sequences that are conserved between the two proteins are shown in FIG. 11. Phosphorylation of nucleoplasmin is believed to increase its translocation to the nucleus and also its activity (Sealy et al. Biochemistry 25: 3064-3072 (1986); Cotten et al. Biochemistry 25:5063-5069 (1986); Vancurova et al. J Cell Sci 108:779-787 (1995); Leno et al. J Biol Chem 271: 7253-7256 (1996)). Similarly, phosphorylation may also alter Npm2 activity. Thus, since both Npm2 and Xenopus laevis nucleoplasm are oocyte (and egg)-specific at the mRNA level and share highest identity, we conclude that Npm2 and nucleoplasmin are orthologs.

EXAMPLE 5

Structure of the Npm2 Gene

Our studies show that all three of the novel oocyte-specific cDNAs have open reading frames. As discussed above, O1-236 is the homolog of Xenopus laevis nucleoplasmin expressed exclusively in eggs.

Figure 12:
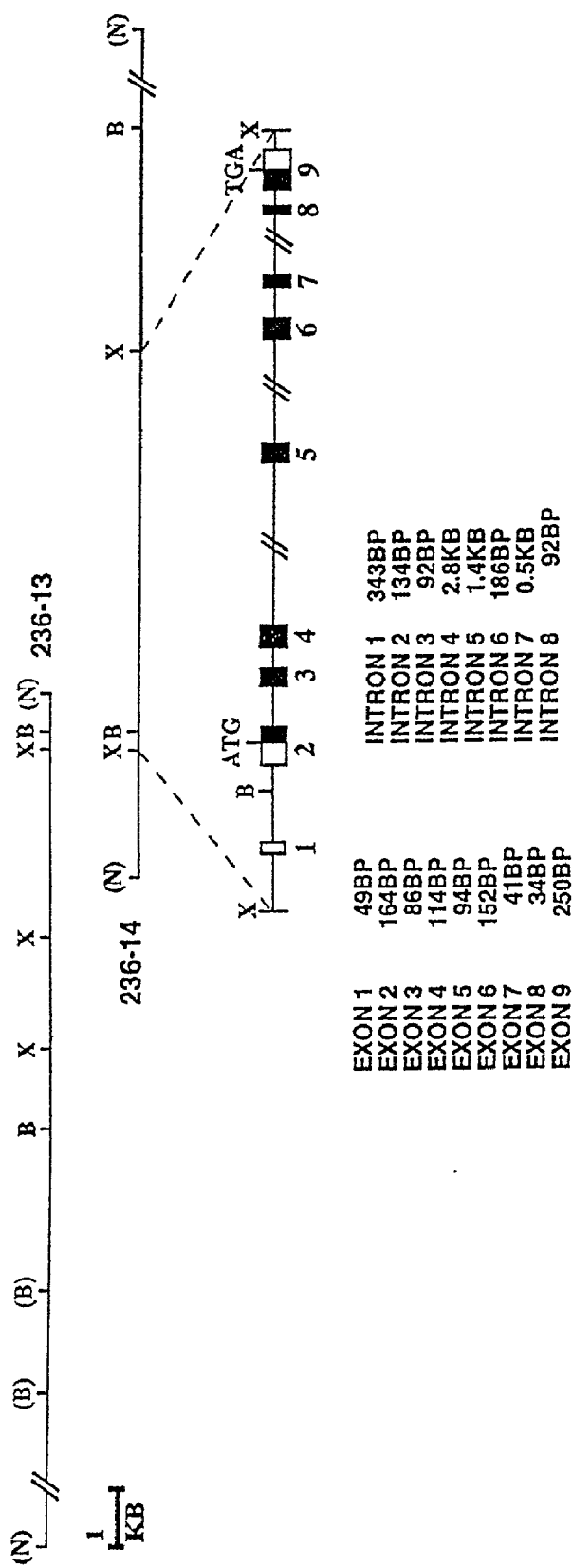
FIG. 12. Structure of the mouse Npm2 gene. Two overlapping recombinant λ clones (236-13 and 236-14), isolated from a mouse 129SvEv library, are shown at the top, and a schematic enlargement of the Npm2 gene is also depicted. Open boxes represent untranslated regions and solid black boxes represent protein coding regions. The 236-13 insert is ~19.0 kb and 236-14 insert is ~21.0 kb. The entire contig is ~37 kb. All 9 exons of the Npm2 gene are encompassed on a single 6.9 kb XbaI (X) fragment as shown. The size of exons and introns are shown at the bottom. Abbreviations: B, BamH1; (B), predicted but unmapped BamH1; (N), NotI from phage cloning site.

One of the full length Npm2 cDNAs (clone 236-1) was used to screen a mouse 129SvEv genomic library (Stratagene) to identify the mouse Npm2 gene. 500,000 phage were screened and 12 positive were identified. Two of these overlapping phage clones, 236-13 and 236-14 (~37 kb of total genomic sequence), were used to determine the structure of the mouse Npm2 gene. The mouse Npm2 is encoded by 9 exons and spans ~6.6 kb (FIGS. 12 and 13A and 13B (SEQ ID NO: 7–14)). Two moderate size introns (introns 4 and 5) contribute the majority of the gene size. The initiation ATG codon resides in exon 2 and the termination codon in exon 9. The splice donor and acceptor sites (FIGS. 13A and 13B (SEQ ID NO: 7–14)) match well with the consensus sequences found in rodents, and all of the intron-exon boundaries conform to the "GT-AG" rule (Senaphthy et al. Methods Enzymol 183:252–278 (1990)). A consensus polyadenylation signal sequence (AATAAA) is found upstream of the polyA tracts which are present in the two isolated cDNAs (FIGS. 13A and 13B (SEQ ID NO: 7–14)).

Analysis of the open reading frames of O1-180 and O1-184, fails to demonstrate any structural motifs reminiscent of known proteins, suggesting that they will be functionally unique. As with O1-236, a λFixII genomic library generated from mouse strain 129SvEv will be used for the isolation of the O1-180 and O1-184 genes. Restriction enzyme digestions, Southern blot analysis, subcloning and sequence analysis will be used to determine the genomic structure including the location and sequence of exons, exon-intron boundaries, and 5' and 3' non-translated regions. This gene structure information will be critical in generating a gene targeting vector as described below. In addition to O1-236, we have cloned 14 mouse genes from this genomic library and aided in the analysis of another 8 genes from this library. Thus, based on our previous experience, the cloning of these mouse genes will be fairly straightforward.

EXAMPLE 6

Chromosomal Mapping of the Mouse Npm2 Gene

Chromosomal mapping of genes in the mouse can identify candidate genes associated with spontaneous or induced mouse mutations. For example, mapping of the TGF-0 family member, growth differentiation factor-5 (GDF-5), showed that it mapped to the same chromosomal location as the gene causing brachypodism in mice. Later studies showed that mutations in GDF-5 cause autosomal dominant brachydactyly type C and two types of recessive chondrodysplasia in humans. To further aid in our functional analysis of the isolated novel ovary-specific cDNAs we are mapping these mouse genes using the Research Genetics Radiation Hybrid Panel. We have mapped several other genes in our laboratory, including O1-186 (Table 3) and therefore we believe that these studies will be fairly straightforward. This information may direct us to known mutations in the mouse mapping to the same chromosomal region associated with reproductive defects. Identification of the syntenic region on the human chromosome may identify one or more of these novel ovarian genes as candidate genes for known human diseases which map to these regions.

To map the mouse Npm2 gene, we used the Research Genetics radiation hybrid panel, The Jackson Laboratory Backcross DNA Panel Mapping Resource, and The Jackson Laboratory Mouse Radiation Hybrid Database. Forward (GCAAAGAAGC CAGTGACCAA GAAATGA) and reverse (CCTGATCATG CAAATTTTAT TGTGGCC) primers within the last exon were used to PCR amplify a 229 bp fragment from mouse but not hamster. Using these primers, the mouse Npm2 gene was mapped to the middle of chromosome 14 (FIG. 14). Npm2 shows linkage to D14Mit32 with a LOD of 11.2 and also has a LOD of 7.8 to D14Mit203. This region is syntenic with human chromosome 8p21.

These studies will be part of our initial efforts to identify novel gene products which may be potential targets for contraceptives or treatment of infertility in human females.

As mentioned above, we have created several mouse models with defects in the ovary. We will also use ovaries from these various models (especially the GDF-9-deficient and FSH-deficient mice) to further study by in situ hybridization any ovary-specific genes. Thus, these additional studies may help to further define the factors which regulate their expression and the roles of these ovary-specific genes in vivo.

EXAMPLE 7

Generation of Knockout Mice Lacking Novel Ovary-Expressed Genes

We will initiate studies to generate knockout mice lacking ovary-specific genes. Using the gene sequences obtained above, we will generate a targeting vector to mutate the O1-180, O1-184 and O1-236 genes in embryonic stem (ES) cells. These targeting vectors will be electroporated into the hprt-negative AB2.1 ES cell line and selected in HAT and FIAU. Clones will be processed for Southern blot analysis and screened using 5' and 3' external probes. ES cells with the correct mutation will be injected into blastocysts to generate chimeras and eventually heterozygotes and homozygotes for the mutant O1-180, O1-184 and O1-236 genes. Based on our success rate of transmission of mutant ES cell lines (28 independent mutant alleles from multiple ES cell lines) we do not anticipate any difficulties in generating heterozygotes and homozygotes for the mutant O1-180, O1-184 and O1-236 alleles.

Since expression of O1-180, O1-184 and O1-236 is limited to the ovary, we anticipate that these O1-180-deficient, O1-184-deficient and O1-236-deficient mice will be viable, but that females lacking these gene products will have fertility alterations (i.e., be infertile, subfertile, or superfertile). Mutant mice will be analyzed for morphological, histological and biochemical defects similar to studies we have performed in the past. These are well within the ability of the person of ordinary skill to carry out, without undue experimentation and are expected to confirm that O1-180, O1-184 and O1-236 are key intraovarian proteins required for folliculogenesis, oogenesis, or fertilization, and that in the absence of these proteins, female mice will have increased or decreased fertility. These studies will lead us to search for human reproductive conditions with similar idiopathic phenotypes.

While this invention has been particularly shown and described with references to preferred embodiment thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically therein. Such equivalents are intended to be encompassed in the scope of the claims.

TABLE 1

Summary of database searches of pO1 cDNA clones

| pO1 cDNA Matches | Number identified | Percentage |
|---|---|---|
| Known Genes | 180 | 54.4% |
| Mouse/Human EST | 120 | 36.2% |
| RARE ESTs (1 EST match) | (8) | (2.4%) |
| ESTs from 2-cell library | (3) | (0.9%) |
| No match | 31 | 9.4% |
| Total | 331 | 100% |

TABLE 2

Analysis of ovarian cDNAs with no known function

| PO1 cDNA | Adult mRNA expression | Upregulated in GDF-9-deficient ovary | Database match | Further studies (in situ hybridization; chromosomal mapping) |
|---|---|---|---|---|
| 24 | Multiple | No | — | No |
| 27 | Multiple | Yes | — | Oocyte-specific by in situ |
| 37 | Multiple | Yes | — | No |
| 70 | Multiple | No | — | No |
| 91 | | | 1 EST (2-cell) | |
| 97 | Multiple | No | ? | No |
| 101 | Multiple | No1 | — | No |
| 114 | Multiple | No | — | No |
| 110 | Multiple | Yes | — | No |
| 126 | Multiple | Yes | — | No |
| 180 | Ovary-specific | Yes | — | Oocyte-specific by in situ |
| 184 | Ovary-specific | Yes | >1 EST (All 2-cell) | Oocyte-specific byin situ |
| 186 | Ovary-specific | Yes | — | Granulosa cell-specific by in situ |
| 223 | Multiple | No | — | No |
| 224 | Multiple | No | — | No |
| 236 | Ovary-specific | Yes | 6 EST (2 c-cell and others) | Oocyte-specific by in situ |
| 255 | Multiple | No | "zinc-finger" domains | |
| 279 | Multiple | No | — | No |
| 317 | Multiple | No | — | No |
| 330 | Multiple | No | — | No |
| 331 | Multiple | No | — | No |
| 332 | Multiple | No | — | No |
| 334 | Multiple | No | — | No |
| 371 | Multiple | No | — | No |

TABLE 3

Analysis of partial or full-length cDNAs

| pO1 cDNA | ORF | DataBase Homolog |
|---|---|---|
| O1-180 | 361 aa | No |
| O1-184 | 426 | No |
| O1-236 | 207 | Yes; Xenopus laevis nucleoplosmin homolog (81% similar) |

What is claimed is:

1. An isolated polynucleotide comprising the polynucleotide sequence set forth in SEQ ID NO: 1.

2. The polynucleotide of claim 1, wherein the polynucleotide is isolated from a mammalian cell.

3. An expression vector comprising the polynucleotide of claim 1.

4. The vector of claim 3, wherein the vector is a plasmid.

5. The vector of claim 3, wherein the vector is a viral vector.

6. A purified host cell containing the vector of claim 3.

7. The host cell of claim 6, wherein the cell is prokaryotic.

8. The host cell of claim 6, wherein the cell is eukaryotic.

9. An isolated polynucleotide that is fully complementary to the polynucleotide sequence of claim 1.

* * * * *